US008810789B2

(12) United States Patent
Zhao et al.

(10) Patent No.: US 8,810,789 B2
(45) Date of Patent: Aug. 19, 2014

(54) THIN LAYER CHROMATOGRAPHY-SURFACED ENHANCED RAMAN SPECTROSCOPY CHIPS AND METHODS OF USE

(71) Applicant: University of Georgia Research Foundation, Inc., Athens, GA (US)

(72) Inventors: Yiping Zhao, Statham, GA (US); Justin L. Abell, Athens, GA (US); Jing Chen, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 72 days.

(21) Appl. No.: 13/670,682

(22) Filed: Nov. 7, 2012

(65) Prior Publication Data

US 2013/0128265 A1 May 23, 2013

Related U.S. Application Data

(60) Provisional application No. 61/556,410, filed on Nov. 7, 2011.

(51) Int. Cl.
*G01J 3/44* (2006.01)
*G01N 21/65* (2006.01)

(52) U.S. Cl.
CPC .. *G01N 21/65* (2013.01); *G01J 3/44* (2013.01)
USPC ............................................. 356/301

(58) Field of Classification Search
CPC ..................................... G01N 21/65
USPC ....................................... 356/301
See application file for complete search history.

(56) References Cited

U.S. PATENT DOCUMENTS

| | | |
|---|---|---|
| 4,874,664 A | 10/1989 | Hamaguchi et al. |
| 5,017,007 A | 5/1991 | Milne et al. |
| 5,780,232 A | 7/1998 | Arlinghaus et al. |
| 5,821,060 A | 10/1998 | Arlinghaus et al. |
| 5,864,397 A | 1/1999 | Vo-Dinh |
| 5,866,204 A | 2/1999 | Robbie et al. |
| 6,002,471 A | 12/1999 | Quake |
| 6,081,328 A | 6/2000 | Eng |

(Continued)

FOREIGN PATENT DOCUMENTS

| | | |
|---|---|---|
| EP | 0261642 A2 | 3/1988 |
| KR | 1020060115368 A | 11/2006 |

(Continued)

OTHER PUBLICATIONS

Caudin et al., Coupling FT Raman and FT SERS microscopy with TLC plates for in situ identification of chemical compounds, Spectrochimica Acta Part A, 1995, 1977-1983, vol. 51, Elsevier Science B.V.

(Continued)

*Primary Examiner* — Tarifur Chowdhury
*Assistant Examiner* — Md Rahman
(74) *Attorney, Agent, or Firm* — Thomas Horstemeyer, LLP

(57) ABSTRACT

The present disclosure includes methods of simultaneous analyte separation and detection using surface enhanced Raman spectroscopy (SERS)-active ultra thin layer chromatography (UTLC) chips. The SERS-active UTLC chips of the present disclosure are used to physically separate compounds within a mixture, which are then identified based on their unique SERS spectra.

24 Claims, 26 Drawing Sheets c. Acquire SERS signal

(56) References Cited

U.S. PATENT DOCUMENTS

| | | | |
|---|---|---|---|
| 6,180,415 | B1 | 1/2001 | Schultz et al. |
| 6,221,154 | B1 | 4/2001 | Lee et al. |
| 6,376,177 | B1 | 4/2002 | Poponin |
| 6,401,526 | B1 | 6/2002 | Dai et al. |
| 7,192,703 | B2 | 3/2007 | Sun et al. |
| 7,267,948 | B2 | 9/2007 | Vo-Dinh |
| 7,274,458 | B2 | 9/2007 | Perez et al. |
| 7,361,313 | B2 | 4/2008 | Chan et al. |
| 7,361,410 | B2 | 4/2008 | Zhang et al. |
| 7,397,558 | B2 | 7/2008 | Kamins et al. |
| 7,400,395 | B2 | 7/2008 | Chan et al. |
| 7,443,489 | B2 | 10/2008 | Natan |
| 7,465,681 | B2 | 12/2008 | Hart et al. |
| 7,485,471 | B1 | 2/2009 | Sun et al. |
| 7,583,379 | B2 * | 9/2009 | Zhao et al. .................... 356/301 |
| 7,656,525 | B2 | 2/2010 | Zhao et al. |
| 7,658,991 | B2 | 2/2010 | Zhao et al. |
| 7,738,096 | B2 | 6/2010 | Zhao et al. |
| 7,879,625 | B1 | 2/2011 | Boss |
| 7,880,876 | B2 | 2/2011 | Zhao et al. |
| 7,889,334 | B2 | 2/2011 | Krause et al. |
| 7,940,387 | B2 | 5/2011 | Dluhy et al. |
| 8,107,070 | B2 | 1/2012 | Zhao et al. |
| 2004/0059279 | A1 | 3/2004 | McWeeney et al. |
| 2004/0074790 | A1 | 4/2004 | Kuremoto et al. |
| 2004/0135997 | A1 | 7/2004 | Chan et al. |
| 2004/0224321 | A1 | 11/2004 | Nicolau et al. |
| 2006/0147927 | A1 | 7/2006 | Geddes et al. |
| 2006/0251874 | A1 | 11/2006 | McClure et al. |
| 2007/0059514 | A1 | 3/2007 | Lee et al. |
| 2007/0140900 | A1 | 6/2007 | Wang et al. |
| 2008/0024776 | A1 | 1/2008 | Bratkovski |
| 2008/0059135 | A1 | 3/2008 | Murugkar et al. |
| 2008/0096005 | A1 | 4/2008 | Premasiri |
| 2010/0085564 | A1 | 4/2010 | Guo et al. |
| 2012/0208722 | A1 | 8/2012 | Dluhy et al. |

FOREIGN PATENT DOCUMENTS

| | | |
|---|---|---|
| WO | 2004059279 A2 | 7/2004 |
| WO | 2004074790 A1 | 9/2004 |
| WO | 2006005111 A1 | 1/2006 |
| WO | 2006066180 A1 | 6/2006 |
| WO | 2006137885 A2 | 12/2006 |
| WO | 2007059514 A2 | 5/2007 |
| WO | 2007124384 A1 | 11/2007 |
| WO | 2007135593 A1 | 11/2007 |
| WO | 2008045114 A2 | 4/2008 |
| WO | 2010073260 | 7/2010 |

OTHER PUBLICATIONS

Roach; Instant, Portable, Similtaneous Pathogen Inspection; Aug. 18, 2006; FoodProductiondaily.com.

Nano Detector Fingers Pathogens; Jul. 26, 2005; FoodProductiondaily.com.

Koglin, et al., "Adsorption and Displacement of Melamine at the Ag/Electrolyte Interface Probed by Surface-Enhanced Raman Microprobe Spectroscopy", J. Phys. Chem 1996, 100, 5078-5089.

Turley, "Fatal Food Fraud", Society of Chemical Industry, C&I Magazine, Issue 8, Apr. 27, 2009.

Hanwen, et al., "The Research Advancement for Analytical Methodology of Melamine and Related Analogues in Environment and Foods", Aug. 1, 2009, vol. 11, No. 8 p. 37.

Mermelstein, "Analyzing for Melamine," Food Technology, Feb. 2009.

Liu, et al., "Potential of SERS for Rapid Detection of Melamine and Cyanuric Acid Extracted from Milk", Springer Science+Business Media, LLC, Jul. 29, 2009.

Cheng, et al., "Screening Melamine Adulterant in Milk Powder with Laser Raman Spectrometry", Journal of Food Composition and Analysis 23 (2010) 199-202.

He, et al., "A New Approach to Measure Melamine, Cyanuric Acid and Melamine Cyanurate Using Surface Enhanced Raman Spectroscopy Coupled with Gold Nanosubstrates", Springer Science+Business Media, LLC, Nov. 16, 2007, p. 66-71.

Lin, et al., "Detection of Melamine in Gluten, Chicken Feed, and Processed Foods Using Surface Enhanced Raman Spectroscopy of HPLC." Toxicology and Chemical Food Safety, vol. 73, No. 8, 2008—Journal of Food Science, pp. 129-135.

Carrillo-Carrion et al., Determination of pesticides by capillary chromatography and SERS detection using a novel Silver-Quantum dots "sponge" nanocomposite, Journal of Chromatography A, 2012, 55-61, vol. 1225, Elsevier B.V.

Koglin et al., Surface Raman Spectra of Nucleic Acid Components Adsorbed at a Silver Electrode, Journal of Molecular Structure, 1980, 421-425, vol. 60, Elsevier Scientific Publishing Company, Amsterdam.

Lucotti et al., TLC-surface enhanced Raman scattering of apomorphine in human plasma, Vibrational Spectroscopy, 2012, 286-291, vol. 62, Elsevier B.V.

Koglin, E., Combining Surface Enhanced Raman Scattering (SERS) and High-Performance Thin-Layer Chromatography (HPTLC), Journal of Molecular Structure, 1988, 369376, vol. 173, Elsevier Science Publishers B.V., Amsterdam.

Carrillo-Carrion et al., Determination of Pyrimidine and Purine Bases by Reversed-Phase Capillary Liquid Chromatography with At-Line Surface-Enhanced Raman Spectroscopic Detection Employing a Novel SERS Substrate Based on ZnS/CdSe Silver-Quantum Dots, Analytical Chemistry, 2011, 9391-9398, vol. 83, ACS Publications.

Trachta et al., Combination of high-performance liquid chromatography and SERS detection applied to the analysis of drugs in human blood and urine, Journal of Molecular Structure, 2004, 175-185, vol. 693, Elsevier B.V.

Jia et al., Multifunctional human serum albumin in the surface-enhanced Raman spectroscopy of porphyrin: demetalation promoter, molecular spacer and stabilizer, Journal of Raman Spectroscopy, 2010, 1615-1620, vol. 41, John Wiley & Sons, Ltd.

Istvan, Krisztina, Selected Applications of Raman and IR Spectroscopy in Chromatography, 2004, 1-13, Institute of Structural Chemistry Chemical Research Center, HAS, Budapest.

Pozzi et al., TLC-SERS study of Syrian rue (*Peganum harmala*) and its main alkaloid constituents, Journal of Raman Spectroscopy, 2012, John Wiley & Sons, Ltd.

Istvan et al., Normal Raman surface enhanced Raman spectroscopic experiments with thin layer chromatography spots of essential amino acids using different laser excitation sources, Spectrochimica Acta Part A, 2003, 1709-1723, vol. 59, Elsevier Science B.V.

SensiQ Technical Notes regarding Affinity Capture Surface for Histidine-Tagged Recombinat Proteins (HisCap and HisHicap CHIPS).

Product Overview of SensiQ pioneer Unparalleled Value in Automated Biomolecular Interaction Analysis.

SensiQ Technical Overview regarding Biomolecular Interaction Analysis.

SensiQ summary sheet.

Wang Y. et al., In situ think layer chromatography-fourier transform-surface-enhanced Raman spectrum study on ingredients of berberine, PubMed, 2002, Abstract, Chemistry Department, Capital Normol University, Beijing 100037, China.

Yakes, et al.; "Detection of *Mycobacterium avium* subsp. paratuberculosis by a Sonicate Immunoassay Based on Surface-Enhanced Raman Scattering"; Clinical and Vaccine Immunology; Vo. 15; Feb. 2008; 8 pgs.

Kim, et al.; Light-Extraction Enhancement of GaInN Light-Emitting Diodes by Graded-Refractive-Index Indium Tin Oxide Anti-Reflection Contact; Adv. Mater. 2008, 20, pp. 801-804.

Zhao, et al.; Enhancing the Sensitivity and Stablility of Biosensors by Novel Nanostructures, 2004. 1-3.

Xu, S. et al. Immunoassay using probe-labelling immunogold nanoparticles with silver staining enhancement via surface-enhanced Raman scattering Analyst, Jan. 2004; 129(1):63-8. Epub Dec. 11, 2003.

(56) References Cited

OTHER PUBLICATIONS

Sastre P., et al. "Comparison of antibodies directed against human respiratory syncytial virus antigens present in two commercial preparations of human immunoglobulins with different neutralizing activities." Vaccine. Dec. 9, 2004;23(4):435-43.
Driskell, J.D., et al. "Low-Level Detection of Viral Pathogens by a Surface-Enhanced Raman Scattering Based Immunoassay" Anal. Chem., 2005, 77 (19), pp. 6147-6154.
Panchuk-Voloshina, N. et al. "Alexa Dyes, a Series of New Fluorescent Dyes that Yield Exeptionally Bright, Photostable Conjugates" Journal of Histochemistry and Cytochemistry, vol. 47, 1179-88, Sep. 1999.
Xu, et al. "Surface-enhanced Raman scattering studies on immunoassay" J. Biomed. Optics 10(3), pp. 031112-1 to 031112-12, (May/Jun. 2005).
Aizpurua, et al; "Optical Properties of Coupled Metallic Nanorods for Field-enhanced Spectroscopy"; The Americal Physical Society; 2005; 13 pgs.
Chaney, et al.; "Aligned Silver Nanorod Arrays Produce High Sensitivity Surface-enhanced Raman Spectroscopy Substrates"; American Institute of Physics; 2005; 3 pgs.
Coldiron, et al.; "Nanotechnology in Cancer"; http://www.concana.com/Nanotechnology.html; Copyright 2007-2008; 5 pgs.
Faulds, et al.; "Evaluation of Surface-enhanced Resonance Raman Scattering for Quantitative DNA Analysis"; http://www.nano-biology.net/showabstract/php?pmid=14719891; 2004; 1 pg.
Gu, et al.; "Optimum Length of Silver Nanorods for Fabrication of Hot Sports"; American Chem. Soc.; 2007; 4 pgs.
Hafner; "Plasmonics: Gold Nanoparticles are Shaped for Effect"; http://www.laserfocusworld.com/articles/article_display.html?id=252462; 2006; 4 pgs.
Kim; "Surface Plasmon Resonances of Noble Metal Nanorods and Nanoparticles"; Sungkyunkwan University; May 29, 2007; 29 pgs.
Murphy, et al.; "Chemical Sensing and Imagining with Metallic Nanorods"; The Royal Society of Chemistry; 2008; 14 pgs.
Nikoobakht, et al.; "Surface-Enhanced Raman Scattering Studies on Aggregated Gold Nanorods"; Am. Chem. Soc.; 2003; 7 pgs.
Shuyi, et al.; "An Approach to Self-Cleaning SERS Sensors by Arraying Au Nanorods on TiO2 Layer"; http://adsabs.harvard.edu/abs/2007SPIE.6647E..13L; 2007; 2 pgs.
Suzuki, et al.; "Physically Self-Assembled Ag Nanorod Arrays for Tunable Plasmonic Sensors"; The Surface Science Society of Japan; 2005; 4 pgs.
Suzuki, et al.; "Vapor Phase Growth of al Whiskers Induced by Glancing Angle Deposition at High Temperature"; American Institute of Physics; 2006; 3 pgs.
Uechi, et al.; "Phtochemical and Analytical Applications of Gold Nanoparticles and Nanorods Utilizing Surface Plasmon Resonance"; Anal Bioanal Chem; 2008; 11 pgs.
Yao, et al.; "A Complementary Study of Surface-Enhanced Raman Scattering and Metal Nanorod Arrays"; Pure Appl. Chem, vol. 72; 2000; 8 pgs.
Yao, et al.; "Electronic Properties of Metal Nanorods Probed by Surface-enhanced Raman Spectroscopy"; Chem. Commun.; The Royal Society of Chemistry; 2000; 2 pgs.
Bentley; "Microsensors: Invisible Watchdogs to Keep Us Safe and Well"; http://www.solve.csiro.au/0805/article1.htm; Aug. 2005; 4 pgs.
Campion, et al.; "Surface-enhanced Raman scattering"; Chemical Society Reviews, vol. 27; 1998; 10 pgs.
Carillo; "Sers nanoparticles; a new optical detection modality for rapid tests"; http://www.cli-online.com/en/featured-articles/sers-nanoparticles-a-new-optical-detection-modality-for-rapid-tests/trackback/1/index.html; Copyright 2004-2007; 4 pgs.
Clin; "Applications of Nanobiotechnology in Clinical Diagnostics"; http://www.clinchem.org/cgi/content/full/53/11/2002; 2007; 1 pg.
Fischer, et al.; "Heightened sense for sensing: recent advances in pathogen immunoassay sensing platforms"; Lawrence Livermore National Laboratory; Feb. 6, 2007; 13 pgs.

Goeller, et al.; Discrimination of Bacterial and Bacteriophages by Raman Spectroscopy and Surface-Enhanced Raman Spectroscopy; Society for Applied Spectroscopy; vol. 61; Nov. 7, 2007; 7 pgs.
Gordon, et al.; "Plasmonic Sensors Based on Nano-Holes: Technology and Integration"; Mico and Nanotechnologies for Speace, Defense and Security II; vol. 6959; 2008; 6 pgs.
Grabar, et al.; "Preparation and Charaterization of Au Colloid Monolayers"; The Pennsylvania State University; vol. 67; Feb. 15, 1995; 9 pgs.
Grow et al.; "Evaluation of the Doodlebug: A Biochip for Detecting Waterborne Pathogens"; http://www.iwapublishing.com/templace.cfm?name=isbn1843396688; Jun. 1, 2003; 1 pg.
Grow et al.; "New biochip technology for label-free detection of pathogens and their toxins"; Biopraxis, Inc.; Journal of Microbiological Methods; 2003; 13 pgs.
Gu, et al.; "Biofunctional magnetic nanoparticles for protein separation and pathogen detection"; ChemComm; Jan. 19, 2006; 9 pgs.
Hou, et al.; "Rapid Chip-Scale Detection by Micro-Spiral Flow and Surface Enhanced Raman Scattering"; http://aiche.confex.com/aiche/2006/techprogram/P66060.HTM; Nov. 15, 2006; 2 pgs.
Kao, et al.; "Surface-Enhanced Raman Detection on Metalized Nanostructured Poly (p-xylylene) Films"; Advanced Materials; 2008; 4 pgs.
Koo, et al.; "Single-molecule detection of biomolecules by surface-enhanced coherent anti-Stokes Raman scattering"; Optics Letters; vol. 30; May 1, 2005; 3 pgs.
Richards; "Nano-optics: Imaging beyond the Diffraction Limit, Fluorescence and Lifetime Modification, Surface Enhanced Raman Scattering"; http://www.opticalproteomics.org/researchnanooptics.php#sers; 1 pg.
Service; "Fast, Sensitive Scan Targets Anthrax"; http://www.sciencemag.org/cgi/content/full/308/5718/45?ck=nck; vol. 308; Apr. 1, 2005; 5 pgs.
Stokes, et al.; "Detection of *E. coli* using a microfluidics-based antibody biochip detection system"; Advanced Monitoring Development Group; Nov. 13, 2000; 7 pgs.
Taurozzi; "Sers-Active Silver Nanoparticle Arrays on Track Etch Membrane Support as Flow-through Water Quality Sensors"; http://aiche.confex.com/aiche/2006techprogram/P59895.HTM; Nov. 15, 2006; 3 pgs.
Vo-Dinh, et al.; "Cancer gene detection using surface-enhanced Raman scattering (SERS)"; Journal of Raman Spectroscopy; Mar. 13, 2002; 6 pgs.
Vo-Dinh; "Biosensors, Nanosensors and Biochips: Frontiers in Environmental and Medical Diagnostics"; Oak Ridge National Laboratory; The 1st International Symposium on Micro & Nano Technology; Mar. 2004; 6 pgs.
Vo-Dinh; "Surface-enhanced Raman Scattering (SERS) Method and Instrumentation for Genomics and Biomedical Analysis"; Journal of Raman Spectroscopy; 1999; 9 pgs.
ARS Project: 408043—Annual Reports for 2004-2007; USDA Agricultural Research Service.
Big Discovery Symposium 2006; UC Santa Barbara; Epigenetic Enzymes and Therapies; slide show.
Kathy Kincade; Raman Spectroscopy: SERS and Silver Nanorods Quickly Reveal Viral Structures; Laser Focus World; Jan. 1, 2007.
Kathy Kincade; Optoelectronic Applications: Nanophotonics—An "Old" Technique Finds New Life in the Nano World; Laser Focus World; Oct. 1, 2006.
Kawai, et al.; Raman Spectroscopic Probes Withstand Hostile Environments; Laser Focus World; Jun. 1, 2005.
Amri, et al.; Adenine and RNA in Mineral Samples. Surface-Enhanced Raman Spectroscopy (SERS) for Picomole Detections; Spectrochimica Acta Part A 59 (2003) pp. 2645-2654.
Stuart, et al.; In Vivo Glucose Measurement by Surface-Enhanced Raman Spectroscopy; Anal. Chem. 2006, 78, pp. 7211-7215.
Faulds, et al.; DNA Detection by Surface Enhanced Resonance Raman Scattering (SERRS); The Royal Society of Chemistry 2005; Analyst, 2005, 130, pp. 1125-1131.
Bell, et al.; Surface-Enhanced Raman Spectroscopy (SERS) for Sub-Micromolar Detection of DNA/RNA Mononucleotides; J. Am. Chem. Soc. 2006, 128, pp. 15580-15581.

(56) References Cited

OTHER PUBLICATIONS

Yun Wei Charles Cao, et al.; Nanoparticles with Raman Spectroscopic Fingerprints for DNA and RNA Detection; Science, 297; 2002; pp. 1536-1540.

Mecham, et al.; Research on Bettering Surveillance of Arboviral Threats, Using West Nile Virus as a Model; USDA Agricultural Research Service; abstract.

Vaeth, et al.; Transition Metals for Selective Chemical Vapor Deposition of Parylene-Based Polymers; Apr. 18, 2000; Chem. Mater, 2000, 12, pp. 1305-1313.

Vaeth, et al.; Use of Microcontact Printing for Generating Selectively Grown Films of Poly (p-phenylen vinylene) and Parylenes Prepared by Chemical Vapor Deposition; Sep. 22, 2000; Langmuir 2000, 16, pp. 8495-8500.

Pursel, et al.; Growth of Sculptured Polymer Submicronwire Assembles by Vapor Deposition; 2005; Polymer 46 (2005) pp. 9544-9548.

Hu, et al.; Fabrication, Characterization, and Application in SERS of Self-Assembled Polyelectrolyte-Gold Nanorod Multilayered Films; Sep. 22, 2005; J. Phys. Chem. B 2005, 109, pp. 19385-19389.

Guo, et al.; Bifunctional Au @pt Hybrid Nanorods; 2007; Journal of Colloid and Interface Science, 315 (2007) pp. 363-368.

Suzuki, et al.; Au Nanorod Arrays Tailored for Surface-Enhanced Raman Spectroscopy; 2007; Analytical Sciences; Jul. 2007, vol. 23; pp. 829-833.

Suzuki, et al.; In-Line Aligned and Bottom-Up Ag Nanorods for Surface-Enhanced Raman Spectroscopy; 2006; Applied Physics Letters; 88, 2003; 2003121 (2006); 3 pages.

Tiwari, et al.; Non-Resonance SERS Effects of Silver Colloids with Different Shapes; 2007; Chemical Physics Letters, 446 (2007).

Chu, et al.; A High Sensitive Fiber SERS Probe Based on Silver Nanorod Arrays; Optics Express; vol. 15, No. 19; Sep. 17, 2007; pp. 12230-12239.

Chu, et al.; Silver Nanorod Arrays as a Surface-Enhanced Raman Scattering Substrate for Foodborne Pathogenic Bacteria Detection; 2008; Applied Spectroscopy, vol. 62, No. 8, 2008; pp. 922-931.

Yao, et al.; Cobalt and Nickel Nanorod Array Electrodes as New SERS Active Substrates; 2007; 2 pages.

Yang, et al.; Aligned Silver Nanorod Arrays for Surface-Enhanced Raman Scattering; 2006; online at www.iop.org/EJ/abstract/0957-4484/17/10/038.

Zhao, et al.; Aligned Copper Nanorod Arrays for Surface-Enhanced Raman Scattering; 2007; online at http://ieeexplore.ieee.org/Xplore/dfdeny.jsp?url=/ie15/4295685/429 . . . .

Wang, et al.; Layer uniformity of glancing angle deposition; Vaccum; vol. 78, Issue 1, Apr. 4, 2005, pp. 107-111.

Schubert, et al.; Nanostruccture fabrication by glancing angle ion beam assisted deposition of silicon; Applied Physics A: Materials Science & Processing; vol. 81, No. 3 / Aug. 2005.

Brett, et al.; Glancing Angle Deposition, An Overview of Thin Films and GLAD; http://www.ece.ualberta.ca/~glad/glad.html; 2006.

International Search Report and Written Opinion dated Oct. 1, 2009.

Zhao, et al.; Designing Nanostructures by Glancing Angle Deposition; Proceedings of SPIE; vol. 5219; Nanotubes and Nanowires; Invited Paper, pp. 59-73.

Katherine A. Willets and Richard P. Van Duyne; Localized Surface Plasmon Resonance Spectroscopy and Sensing; Annual Review of Physical Chemistry; vol. 58: 267-297 (Vol. publication date May 2007); First published online as a Review in Advance on Oct. 26, 2006.

SensiQ Technical Notes regarding Vescile Capture for Membrane Bound Receptor Interactions (VesCap CHIP).

Science, vol. 319, pp. 1163; Materials Science/A Graded Improvement; Adv. mater, 20, pp. 801-804; (2008).

K. Robbie, et al.; Sculptured Thin Films and Glancing Angle Deposition: Growth Mechanics and Applications; J. Vac. Sci. Technol. A 15 (3), May/Jun. 1997; pp. 1460-1465.

K. Robbie, et al.; Fabrication of Thin Films with Highly Porous Microstructures; J. Vac. Sci. Technol. A 13(3), May/Jun. 1995; pp. 1032-1035.

K. Robbie, et al.; First Thin Film Realization of a helicoidal Bainisotropic Medium; J. Vac. Sci. Technol. A 13(6), Nov./ Dec. 1995; pp. 2991-2993.

Huang, et al; Single-Domain Antibody-Conjugated Nanoaggregate-Embedded Beads for Targeted Detection of Pathogenic Bacteria; Chem. Eur. J. 2009, pp. 1-6.

Gish, et al.; Evaluation of Silver Nanostructures Fabricated Using Glancing Angle Deposition as Localized Surface Plasmon Resonance Biosensors; The Nanotechnology Conference and Trade Show; Boston, Jun. 1-5, 2008; abstract.

SensiQ Technical Notes regarding Avidin-Biotin Based Immobilization (bioCap and AvCap CHIPS).

SensiQ Technical Notes regarding Immobilization by Amine Coupling (COOH1 & COOH2 Chips).

SensiQ Pioneer Capabilities.

Prokes, et al.; Enhanced Plasmon Coupling in Crossed Dielectric/Metal Nanowire Composite Geometries and Applications to Surface-Enhanced Raman Spectroscopy; Appl. Physc. Lett; 90; 2007; 3 pages.

D. Keith Roper; Determining Surface Plasmon Resonance Response Factors for Deposition onto Three-Dimensional Surfaces; Chemical Engineering Science; 62; 2007; pp. 1988-1996.

Takemoto, et al.; A Surface Plasmon Resonance Assay for the Binding of Influenza Virus Hemagglutinin to its Sialic Acid Receptor; Virology; 217; 452-458 (1996) Artide No. 0139.

Hardy, et al.; Valency of Antibody Binding to Enveloped Virus Particles as Determined by Surface Plasmon Resonance; Journal of Virology; Jan. 2003; p. 1649-1652; vol. 77, No. 2.

List from SensiQ/Surface Chemistries—Discover SensiQ.com listting the following 9 documents describing the SensiQ System.

Product Overview of SensiQ Biomolecular Interaction Analysis.

\* cited by examiner

THIN LAYER CHROMATOGRAPHY-SURFACED ENHANCED RAMAN SPECTROSCOPY CHIPS AND METHODS OF USE

CROSS-REFERENCE TO RELATED APPLICATION

This application claims priority to U.S. provisional application entitled "Thin Layer Chromatography-Surface Enhanced Raman Spectroscopy Chips and Methods of Use," having Ser. No. 61/556,410 filed on Nov. 7, 2011, which is entirely incorporated herein by reference.

STATEMENT REGARDING FEDERALLY SPONSORED RESEARCH OR DEVELOPMENT

Aspects of this disclosure may have been made with government support under USDA CSREES Grant #2009-35603-05001, awarded by the U.S. Department of Agriculture. The government may have certain rights in the invention(s).

BACKGROUND

Surface enhanced Raman spectroscopy (SERS) is a highly sensitive detection platform for chemical and biological agents due to the enhancement of the Raman scattering in close vicinity (<10 nm) of nanostructured metal surfaces. In most cases, this technique has been used to identify a single component analyte, or an analyte that has unique peak locations that are different from the background. For real applications, such as detecting particular chemical and biological agents from clinically relevant samples, the mixture could generate a complicated SERS spectrum. The abundance of spectral information in the spectrum makes extracting individual spectral components from that of a mixture a challenge for real-world applications of SERS. Multivariate analyses, e.g., principle component analysis (PCA), are commonly utilized to classify complex SERS spectra and/or distinguish individual components from mixtures. However, difficulties in establishing a complete library of all possible combinations of analytes of interest necessary for building statistical models, as well as in precluding interference from fluctuating environmental contaminants has posed major obstacles for this strategy. In order for SERS to be applied in more realistic situations, a simple means to physically separate the components of a mixture sample prior to SERS detection is necessary.

Thin-layer chromatography (TLC) is a well-established method used for separating components from mixtures. This method is simple and can be used to process multiple samples and standards simultaneously. In TLC the test sample is first spotted onto a thin layer of porous stationary phase (e.g., $SiO_2$ gel) and allowed to dry. During plate development, the mobile phase (i.e., mixture of organic solvents) propagates along the TLC plate via capillary action, allowing the individual components to migrate along the solvent migration direction and spatially redistribute as a function of their varying affinity between the stationary and mobile phases. The separated components are identified by comparing the retention factors ($R_f$, the distance travelled by a component divided by the distance travelled by the solvent) with that of standards, or by coupling with gas chromatography (GC), infrared spectroscopy (IR), nuclear magnetic resonance (NMR), or mass spectrometry (MS), but the procedures involved are time-consuming and labor-intensive.

SUMMARY

Embodiments of the present disclosure include thin layer chromatography (TLC) surface enhanced Raman spectroscopy chips and methods of using the chips.

Briefly described, embodiments of the present disclosure include a method of simultaneous analyte separation and detection in a sample comprising providing a SERS-active UTLC chip, where the SERS-active UTLC chip comprises an array of nanostructures on a surface of a substrate, applying at least one sample comprising at least one analyte to the SERS-active UTLC chip, acquiring at least one SERS spectra for each sample at the sample origin on the chip, immersing at least a portion of the SERS-active UTLC chip in a mobile phase solvent, where the at least one sample is above the mobile phase solvent, developing the chip so that the at least one analyte is physically separated, acquiring at least one SERS spectra for each sample along an UTLC development direction, and analyzing all of the SERS spectra to identify the at least one analyte in each sample.

Embodiments of the present disclosure also include a surface-enhanced Raman spectroscopic (SERS)-active ultra thin layer chromatography (UTLC) chip comprising a UTLC substrate, where the UTLC substrate comprises an array of nanostructures on a surface of a substrate.

Embodiments of the present disclosure include a method of separating and identifying at least one component in a mixture comprising applying the mixture to a SERS-active UTLC chip, where the SERS active UTLC chip comprises an array of Ag nanorods on a surface of a substrate, where a tilt angle β between an individual nanorod and the substrate surface is less than about 90 degrees, acquiring at least one SERS spectra at the origin of application, immersing the SERS-active UTLC chip into a mobile phase solvent, developing the chip so that the components in the mixture are separated and retained at different locations on the chip as a result of their different affinities to the Ag nanorods and solvent, acquiring at least one SERS spectra at intervals along the development direction, and analyzing all of the SERS spectra to identify the at least one component.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

The patent or application file contains at least one drawing executed in color. Copies of this patent or patent application publication with color drawing(s) will be provided by the Office upon request and payment of the necessary fee.

FIGS. 17A-17B are graphs that illustrate SERS spectra of dialysis HeV and sucrose_dil as a function of distance d from the original droplet spot on the AgNR SERS substrate. The symbols * and ♦ denotes the peaks for sucrose_dil and HeV, respectively. Starting from bottom d=0, 0.5 mm, 1.5 mm, so on.

DETAILED DESCRIPTION

Figure 1A:
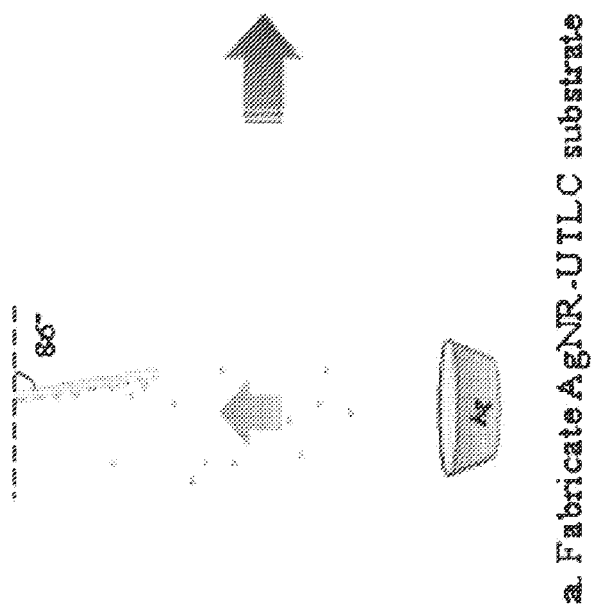
FIGS. 1A-1E are a schematic representation that illustrates an embodiment of the method of simultanteous analyte separation and detection of the present disclosure.
Figure 1B:
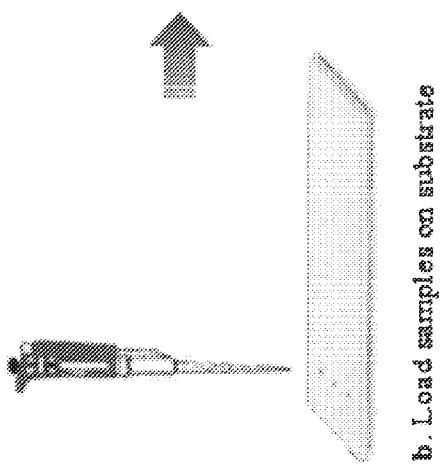
Figure 1C:
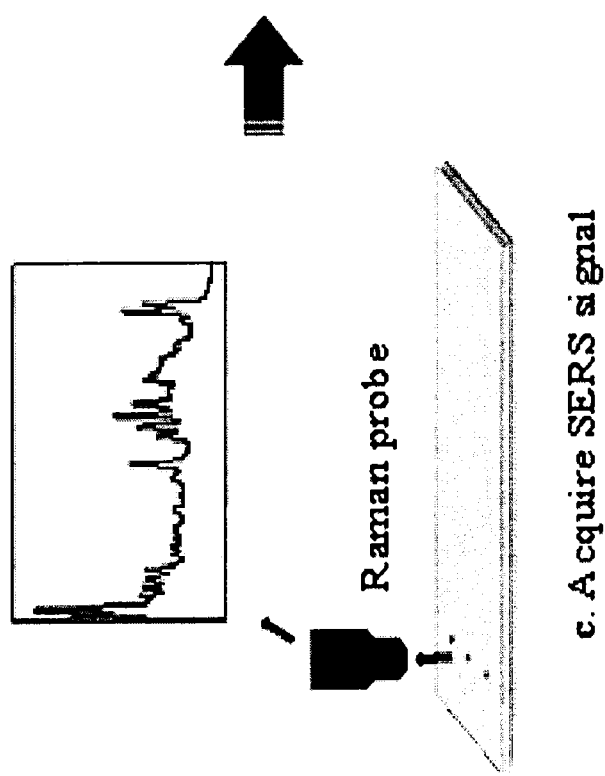
Figure 1D:
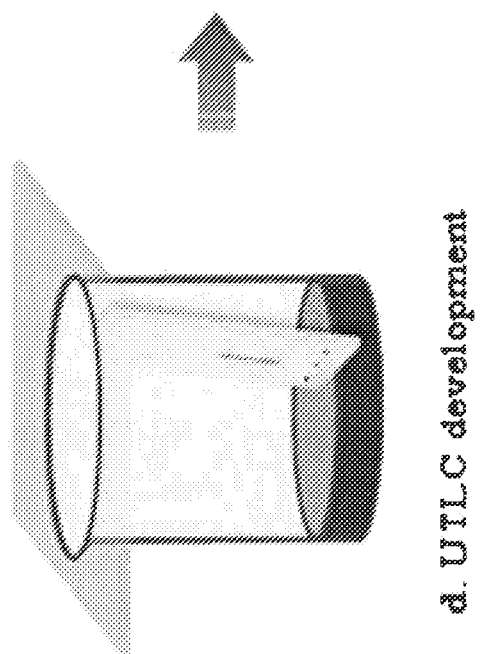
Figure 1E:
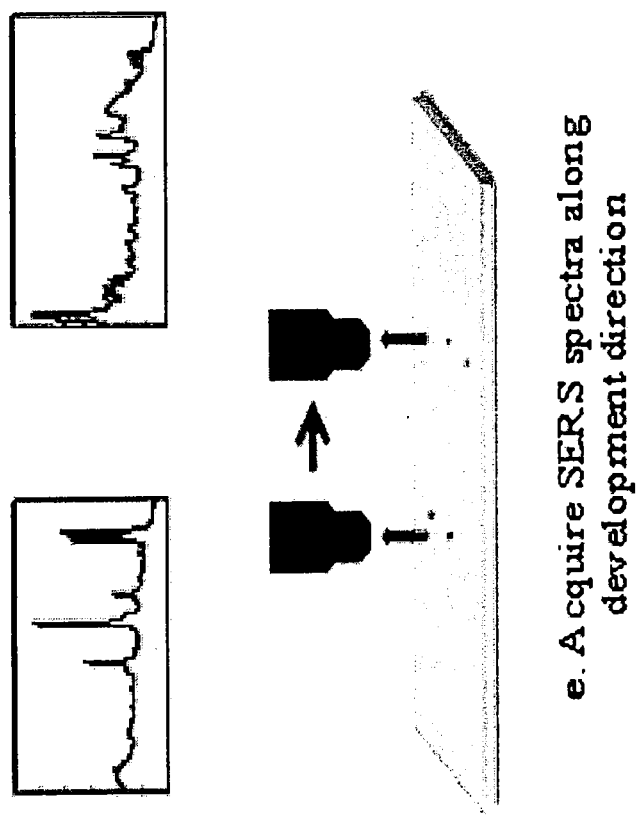

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

DEFINITIONS

Use of the phrase "biomolecule" is intended to encompass deoxyribonucleic acid (DNA), ribonucleic acid (RNA), nucleotides, oligonucleotides, nucleosides, proteins, peptides, polypeptides, selenoproteins, antibodies, combinations thereof, and the like. In particular, the biomolecule can include, but is not limited to, naturally occurring substances such as polypeptides, polynucleotides, lipids, fatty acids, glycoproteins, carbohydrates, fatty acids, fatty esters, macromolecular polypeptide complexes, vitamins, co-factors, whole cells, eukaryotic cells, prokaryotic cells, microorganisms such as viruses, bacteria, protozoa, archaea, fungi, algae, spores, apicomplexan, trematodes, nematodes, mycoplasma, or combinations thereof.

The biomolecule may be a virus, including, but not limited to, RNA and DNA viruses. In particular the biomolecule is a virus, which may include, but is not limited to, negative-sense and positive-sense RNA viruses and single stranded (ss) and double stranded (ds) DNA viruses. The ds group I DNA viruses include the following families: Adenoviridae, Herpesviridae, Papillomaviridae, Polyomaviridae, Poxviridae, and Rudiviridae. The group II ssDNA viruses include the following families: Microviridae, Geminiviridae, Circoviridae, Nanoviridae, and Parvoviridae. The ds group III RNA viruses include the following families: Birnaviridae and Reoviridae. The group IV positive-sense ssRNA virus families: Arteriviridae, Coronaviridae, Astroviridae, Caliciviridae, Flaviviridae, Hepeviridae, Picornaviridae, Retroviridae and Togaviridae. The group V negative-sense ssRNA virus families: Bornaviridae, Filoviridae, Paramyxoviridae, Rhabdoviridae, Arenaviridae, Bunyaviridae, and Orthomyxoviridae. In particular embodiments the biomolecule can be one of a number of strands of the virus and/or a mutated version of a virus or of one of a number of strands of a virus. In particular, the virus can include, but is not limited to, Rotavirus.

In another aspect, the biomolecule is bacteria. The terms "bacteria" or "bacterium" include, but are not limited to, Gram positive and Gram negative bacteria. Bacteria can include, but are not limited to, *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobospirillum, Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella, Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Gemella, Globicatella, Gordona, Haemophilus, Hafnia, Helicobacter, Helococcus, Holdemania lgnavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Phytoplasma, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea Roseomonas, Rothia, Ruminococcus, Salmonella, Selenomonas, Serpulina, Serratia, Shewenella, Shigella, Simkania, Slackia, Sphingobacterium, Sphingomonas, Spirillum, Spiroplasma, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia,* and *Yokenella.* Other examples of bacterium include *Mycobacterium tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies *paratuberculosis, Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides,* and other *Nocardia* species, *Streptococcus viridans* group, *Peptococcus* species, *Peptostreptococcus* species, *Actinomyces israelii* and other *Actinomyces* species, and *Propionibacterium acnes, Clostridium tetani, Clostridium botulinum,* other *Clostridium* species, *Pseudomonas aeruginosa,* other *Pseudomonas* species, *Campylobacter species, Vibrio cholera, Ehrlichia species, Actinobacillus pleuropneumoniae, Pasteurella haemolytica, Pasteurella multocida,* other *Pasteurella* species, *Legionella pneumophila,* other *Legionella* species, *Salmonella typhi,* other *Salmonella* species, *Shigella* species *Brucella abortus,* other *Brucella* species, *Chlamydi trachomatis, Chlamydia psittaci, Coxiella burnetti, Escherichia coli, Neiserria meningitidis, Neiserria gonorrhea, Haemophilus influenzae, Haemophilus ducreyi,* other *Hemophilus* species, *Yersinia pestis, Yersinia enterolitica,* other *Yersinia* species, *Escherichia coli, E. hirae* and other *Escherichia* species, as well as other *Enterobacteria, Brucella abortus* and other *Brucella* species, *Burkholderia cepacia, Burkholderia pseudomallei, Francisella tularensis, Bacteroides fragilis, Fudobascterium nucleatum, Provetella* species, and *Cowdria ruminantium,* or any strain or variant thereof.

The term biomolecule may also refer to drugs such as anabolic agents, peptide hormones, growth factors and related substances, beta-2 agonists, hormone and metabolic modulators, diuretics and other masking agents and mycrotoxins such as aflatoxin B1, T-2, ZEA, DON, FUM B1, ergotamine, lolitrom-B, etc.

The term biomolecule may also refer to a surface molecule or surface antigen on the surface of a pathogen (e.g., a bacterial cell), or the biomolecule is a toxin or other byproduct of a pathogen (e.g., a toxin produced by a bacterial cell). Other examples of biomolecules are viral projections such as Hemagglutinin and Neuraminidase.

Use of the phrase "peptides", "polypeptide", or "protein" is intended to encompass a protein, a glycoprotein, a polypeptide, a peptide, and the like, whether isolated from nature, of viral, bacterial, plant, or animal (e.g., mammalian, such as human) origin, or synthetic, and fragments thereof. A preferred protein or fragment thereof includes, but is not limited to, an antigen, an epitope of an antigen, an antibody, or an antigenically reactive fragment of an antibody.

Use of the phrase "polynucleotide" is intended to encompass DNA and RNA, whether isolated from nature, of viral, bacterial, plant or animal (e.g., mammalian, such as human) origin, synthetic, single-stranded, double-stranded, comprising naturally or non-naturally occurring nucleotides, or chemically modified.

Discussion:

In accordance with the purpose(s) of the present disclosure, as embodied and broadly described herein, embodiments of the present disclosure, in one aspect, relate to thin layer chromatography (TLC) surface-enhanced Raman spectroscopy (SERS) chips (e.g., plates) and methods of use. In particular, oblique angle deposition (OAD)-generated Ag nanorod (NR) films demonstrate significant capillary behavior due to their high porosity and hydrophilic nature. In embodiments of the present disclosure, the AgNR films can therefore be used to physically separate compounds within a mixture as a TLC plate. Such TLC separation capabilities are very advantageous when coupled with the intrinsic capability for direct and high sensitivity chemical (SERS) detection.

Silver nanorod (AgNR) arrays fabricated by oblique angle deposition (OAD) have anisotropic nanoporous structures with the nanorod diameters under about 100 nm in at least two dimensions, and can be readily used as SERS-active substrates. The AgNR arrays also possess the requisite high porosity to be utilized as an ultra-thin layer chromatography (UTLC) plate. Hence, the simultaneous separation and detection of components in complex mixtures is achieved in embodiments of the present disclosure on this type of platform.

In an embodiment, disclosed herein is the use of AgNR array substrates fabricated by oblique angle deposition (OAD) for simultaneous on-chip separation of mixtures through ultra-thin layer chromatography (UTLC) and detection by surface enhanced Raman spectroscopy (SERS). The mixture samples are spotted onto the ULTC-SERS chip, which is then immersed into mobile phase solvents. As the capillary force drives the mobile phase to migrate towards the development direction, the components in the mixture are separated and retained at different locations on the chip as a result of their different affinities to the silver surface and the solvents. A Raman probe is used to scan the chip and spatially-resolved SERS spectra are obtained. Owing to the highly uniform SERS response across the entire substrate, the intensity of characteristic peaks can be used as an indication of surface density of specific components.

Embodiments of the present disclosure include a method of simultaneous analyte separation and detection in a sample comprising fabricating a SERS-active UTLC chip, where the SERS-active UTLC chip comprises an array of nanostructures on a surface of a substrate, applying at least one sample comprising at least one analyte to the SERS-active UTLC chip, acquiring at least one SERS spectra for each sample at the sample origin, immersing at least a portion of the SERS-active UTLC chip in a mobile phase solvent, where the at least one sample is above the mobile phase solvent, developing the chip so that the at least one analyte is physically separated, acquiring at least one SERS spectra for each sample along an UTLC development direction, and analyzing all of the SERS spectra to identify the at least one analyte in each sample.

In an embodiment of the present disclosure, the array of nanostructures comprise Ag nanorods fabricated by oblique angle deposition (OAD). In another embodiment, the OAD fabrication comprises rotating the substrate in a polar direction relative to a vapor arrival line of a vapor flux of a material to achieve a desired incident angle between the vapor arrival line and the substrate, optionally rotating the substrate azimuthally, exposing at least a portion of the surface of the substrate to the vapor flux of a material at the desired incident angle, and forming the array of nanorods on the surface of the substrate. In another embodiment, the substrate is planar, an incident angle $\phi$ is defined by the vapor arrival line and the surface normal of the planar substrate, and $\phi$ is greater than about 75°. In another embodiment, the substrate is flexible and/or nonplanar (e.g., the substrate is plastic and can be folded, e.g., into a cylindrical shape).

In an embodiment of the present disclosure, the nanostructures are fabricated by glancing angle deposition (GLAD). In another embodiment, GLAD generates vertical nanorods by azimuthal rotation.

In an embodiment of the present disclosure, the substrate comprises a nanostructure substrate. The nanostructures can include, but are not limited to, nanorods, nanowires, nanotubes, nanospirals, combinations thereof, and the like, and uniform arrays of each. The nanostructures (e.g., nanorods) can be fabricated of one or more materials such as, but not limited to, a metal, a metal oxide, a metal nitride, a metal oxynitride, a metal carbide, a doped material, a polymer, a multicomponent compound, a compound (e.g., a compound or precursor compound (organic or inorganic compound) including a metal, a metal oxide, a metal nitride, a metal oxynitride, a metal carbide, a doped material), and combinations thereof. The metals can include, but are not limited to, silver, nickel, aluminum, silicon, gold, platinum, palladium, titanium, copper, cobalt, zinc, other transition metals, composites thereof, oxides thereof, nitrides thereof, silicides thereof, phosphides ($P^{3-}$) thereof, oxynitrides thereof, carbides thereof, and combinations thereof. In particular the materials can include one or more of the following: silver, gold, nickel, silicon, germanium, silicon oxide, and titanium oxide. The composition of the nanostructures is the same as that of the materials described herein or a combination of the materials described herein, or alternative layers of each. In another embodiment, the composition of the nanostructures comprises a silver nanorod "core" with a gold "shell" coating the entire nanorod (e.g., a "core-shell" nanorod structure). In another embodiment, the gold "shell" coats only a portion of the Ag nanorod.

In an embodiment of the SERS substrate of the present disclosure, the nanostructure is a nanorod. In particular embodiments, the nanorod is formed in a uniform and aligned array on the substrate. The nanorod can have the dimensions and characteristics as described below. In particular, the nanorods (e.g., silver, nickel, silicon, and titanium oxide) are disposed on a planar substrate, such a glass or silicon slide or disk, or a non-planar substrate, such as an optical fiber, or other cylindrically symmetric substrates.

The length is the largest dimension of the nanostructure and is the dimension extending from the substrate. The length/height of the nanorod can be from a few hundred nanometers or less to over a few thousand nanometers. In embodiments, the nanostructure can have a length of about 10 nm to 10,000 nm, about 10 nm to 5,000 nm, about 10 nm to 4,000 nm, about 10 nm to 3,000 nm, about 10 nm to 2,000 nm, about 10 nm to 1,000 nm, about 10 nm to 500 nm, about 10 nm to 250 nm, about 10 nm to 100 nm, and about 10 nm to 50 nm. In particular, the nanostructures can have a length of about 100 nm to about 1,500 nm. The length depends, at least in part, upon the deposition time, deposition rate, and the total amount of evaporating materials. The substrate can have nanorods of the same height or of varying heights on one or more portions of the substrate.

The diameter is the dimension perpendicular to the length. The diameter of the nanostructure is about 10 to 30 nm, about 10 to 60 nm, about 10 to 100 nm, about 10 to 150 nm. In particular, the nanorods can have a diameter of about 50 to 120 nm. One or more of the dimensions of the nanostructure could be controlled by the deposition conditions and the materials.

The substrate can have from tens to tens of thousands or more nanorods formed on the substrate. The array of nanostructures can be defined as having a distance of about 10 to 30 nm, about 10 to 60 nm, about 10 to 100 nm, about 10 to 150 nm, and about 10 to 200 nm, between each of the nanostructures. Alternatively, the array of nanostructures can be defined as having an average density of about 11 to 2500/$\mu m^2$. The number of nanorods, height and diameter of the nanorods, and the material that the nanorods are fabricated of will depend upon the specific application of the SERS system.

In an embodiment, the Ag nanorod substrate fabrication comprises oblique angle deposition (OAD) fabrication. Additional details regarding the fabrication of Ag nanorod substrates by OAD method can be found, e.g., in U.S. Pat. Nos. 7,658,991, 7,738,096 and 7,583,379, each of which are incorporated herein by reference in their entireties.

Embodiments of the present disclosure include a method of simultaneous analyte separation and detection in a sample where the sample is selected from a buccal cell, a buffered solution, saliva, sweat, tear, phlegm, urine, blood, plasma, serum, breath condensate, cerebrospinal fluid, lymph, a cell, a microorganism, a wash from vegetables, a wash from fruits, a fluid with mixed components such as a polluted water sample, a meat sample, a combination thereof, and an aqueous dilution thereof. In an embodiment, the analyte is selected from melamine, a contaminant, a biomarker, a polypeptide, a protein, a glycoprotein, a nucleic acid, a eukaryotic cell, a prokaryotic cell, a virus, a bacterium, a protozoan, a apicomplexan, a trematode, a nematode, a fungus, a spore, a carbohydrate, a lipid, a vitamin, and a combination thereof. In another embodiment, the method includes simultaneous separation and detection of a biomolecule. In another embodiment, the analyte comprises at least one compound within a mixture.

Embodiments of the present disclosure include a method of simultaneous analyte separation and detection where the SERS-active UTLC chip is patterned with at least one channel so that each sample is applied in its own channel to avoid cross contamination.

In an embodiment of the present disclosure, the mobile phase solvent is selected from methanol, acetonitrile, hexanes, hexanol, ethanol, propanol, isopropanol, chloroform, dichloromethane, acetone, ethyl ether, ethyl acetate, toluene, chlorobenzene, tetrahydrofuran, dimethyl sulfoxide, water, and any combination thereof.

In an embodiment of the present disclosure, the sample is applied near the edge (e.g., bottom) of the chip, which is the sample origin. In another embodiment, the sample is applied about 1 mm to about 10 mm from the edge (e.g., bottom) of the chip. In another embodiment, the sample is applied about 5 to about 10 mm from the bottom of the chip.

In an embodiment of the present disclosure, the SERS spectra are obtained at regular intervals along the developing direction. In an embodiment, the SERS spectra are obtained at about every 0.5 mm along the developing direction, beginning at about 5 mm below the sample origins until about 1 mm beyond the identified solvent front. In another embodiment, the SERS spectra are obtained at regular intervals of about 0.25 to 1 mm along the developing direction. In another embodiment, the SERS spectra are obtained at irregular intervals along the developing direction.

Embodiments of the present disclosure include a method of simultaneous detection and separation of an analyte in a sample where analyzing all of the SERS spectra comprises dividing the peak intensities obtained at intervals each by the highest peak intensity to yield a series of normalized peak intensities, where the series of normalized peak intensities are plotted against a developing distance. In an embodiment, the at least one analyte is separated by the UTLC and identified based on its signature SERS peak.

Embodiments of the present disclosure include a surface-enhanced Raman spectroscopic (SERS)-active ultra thin layer chromatography (UTLC) chip comprising a UTLC substrate, where the UTLC substrate comprises an array of nanostructures on a surface of a substrate. In an embodiment, the array of nanorods comprise Ag nanorods where a tilt angle $\beta$ between an individual nanorod and the substrate surface is less than about 90 degrees. In another embodiment, the array of nanorods are selected from Ag nanorods, dielectric coated Ag nanorods, surface modified Ag nanorods, and any combination thereof.

Embodiments of the present disclosure include a SERS-active UTLC chip where the array of nanorods includes nanorods of substantially the same height. In an embodiment, the array of nanorods includes nanorods of a plurality of heights. In another embodiment, the array of nanorods includes nanorods of a plurality of diameters. In yet another embodiment, the array of nanorods includes nanorods of substantially the same diameter.

Embodiments of the present disclosure include a method of separating and identifying at least one component in a mixture comprising applying the mixture to a SERS-active UTLC chip, where the SERS active UTLC chip comprises an array of Ag nanorods on a surface of a substrate, where a tilt angle $\beta$ between an individual nanorod and the substrate surface is less than about 90 degrees, acquiring at least one SERS spectra at the origin of application, immersing the SERS-active UTLC chip into a mobile phase solvent, developing the chip so that the components in the mixture are separated and retained at different locations on the chip as a result of their different affinities to the Ag nanorods and solvent, acquiring at least one SERS spectra at intervals along the development direction, and analyzing all of the SERS spectra to identify the at least one component.

EXAMPLES

Example 1

Oblique angle deposition (OAD)-generated Ag nanorod (AgNR) films demonstrate significant capillary behavior due to their high porosity and hydrophilic nature. The AgNR films can therefore be used to physically separate compounds within a mixture as a thin layer chromatography (TLC) substrate. Such TLC separation capabilities are very advantageous when coupled with the intrinsic capability for direct and high sensitivity chemical surface enhanced Raman spectroscopy (SERS) detection.

EXPERIMENTAL

Materials
Methyl Orange (4-dimethylaminoazobenzene-4'-sulfonic acid sodium acid) and Cresol Red (o-Cresolsulfonephthalein), were obtained from Alfa Aesar (Ward Hill, Mass.). Trans-1,2-bis(4-pyridyl)ethylene (BPE) was purchased from Fluka (Buchs, Switzerland). Melamine (1,3,5-triazine-2,4,6-triamine), Rhodamine 6G, melamine, acetonitrile, and sodium sulphate ($Na_2SO_4$) were products of Sigma-Aldrich (St. Louis, Mo.). Methanol was obtained from J. T. Baker (Phillipsburgm N.J.). Silver (99.999%) and titanium (99.995%) were obtained from Kurt L. Lesker (Clairton, Pa.).

UTLC-SERS Plate Fabrication

The SERS-active UTLC plates were fabricated using the OAD technique in a custom-built electron beam evaporation system (Torr International, New Windsor, N.Y.) as previously described[1]. Microscopic glass slides were cleaned with Piranha solution (80% sulfuric acid, 20% hydrogen peroxide), rinsed with deionized (DI) water, and dried with compressed nitrogen gas before being loaded into the evaporation system. A 20-nm Ti layer and a 200-nm Ag layer were first deposited onto the glass substrates at normal incidence angle at the rates of 0.2 nm/s and 0.3 nm/s, respectively. The substrates were then rotated to 86° with respect to the vapor incident direction before the Ag vapor influx continued to deposit on the substrates at a rate of 0.3 nm/s. The chamber maintained a pressure of $10^{-6}$ Torr during all depositions. The last oblique angle deposition step resulted in an array of Ag nanorods (AgNRs) 868±95 nm in length, and 99±29 nm in diameter, with a tilting angle of approximately 73° with respect to the substrate normal[2].

UTLC Process

The as-deposited AgNR substrates were marked with tweezer tips at the edges to indicate the sample origin locations, and then cleaned using 40 W high RF setting with a constant flow of ultra-pure argon for 2 min. Argon plasma cleaning allowed the removal of carbonaceous and organic contaminants during fabrication and storage of the substrates[3].

After plasma cleaning, 0.1 µL of each sample were spotted onto the indicated sample origins, and the SERS spectra were acquired immediately after the droplets were dried at ambient temperature. The UTLC-SERS substrate was then placed into a glass beaker saturated with the mobile phase solvent 30 min prior to plate development. The development process took 5 min for each plate, and remained under saturated mobile phase vapor pressure with the help of a glass lid.

For the UTLC of melamine and Rhodamine 6G, two concentrations of melamine ($1 \times 10^{-2}$ M and $10^{-4}$ M) and their mixtures with $10^{-4}$ M Rhodamine 6G were investigated. Methanol was used as the developing solvent. For the separation of Methyl Orange, Cresol Red, and BPE (each at a concentration of $10^{-4}$ M), a mixture of methanol: acetonitrile: 5% $Na_2SO_4$ aqueous solution (3:3:10) was used as the mobile phase.

Proceeding UTLC development, the solvent front position was marked immediately after the substrate was taken out of the beaker, and before it was being gently dried with nitrogen.

SERS Measurement

SERS spectra were acquired using a HRC-10HT Raman analyzer system (Enwave Optronics, Irvine, Calif.) equipped with a 785 nm diode laser, a spectrometer, an integrated Raman probe for both excitation and collection, and separate delivery and collection fibers. The focal length of the Raman probe was 6 mm and the diameter of the laser beam was 100 µm. The laser power used in all measurements was 30 mW at the sample, as monitored with a power meter. Integration time for exposure varied from 1 s to 10 s for different samples to yield optimal SERS intensity.

Before UTLC, nine spectra were collected from each sample spot at the origin. After UTLC, spectra were acquired at an interval of 0.5 mm along the developing direction, starting from 5 mm below the sample origins until approximately 1 mm beyond the identified solvent front.

Renishaw Mapping

For the UTLC of melamine and Rhodamine 6G, the developed plate was mapped using a Renishaw Invia Raman system (Renishaw, Hoffman Estates, Ill.) with an excitation wavelength of 785 nm, 5.5 mW power, and an acquisition time of 10 s for each spectrum. The Raman probe was programmed to move across the plate and collect SERS spectra from each pixel, with a step size of 200 µm.

Data Analysis

The collected SERS spectra were analyzed with the WiRE 2.0 (Renishaw, Hoffman Estates, Ill.) and Origin 8.0 (OriginLab, Northampton, Mass.) software. Specific peaks for each analyte were fitted to obtain corresponding peak intensity, as an indicator of local concentration. The spectra acquired by the Enwave Raman system were proof-read manually and peak intensity for locations where discrepancies with the actual spectra existed were reset to zero, and only the peak intensity data for the recognizable spectra remained for subsequent analysis.

For each sample, the peak intensities at various locations along the development direction were divided by the highest peak intensity found in that sample, resulting in a series of relative peak intensities, which were plotted against the developing distance to generate the corresponding chromatograms.

Results and Discussion

Solvent Characterization

Figure 2:
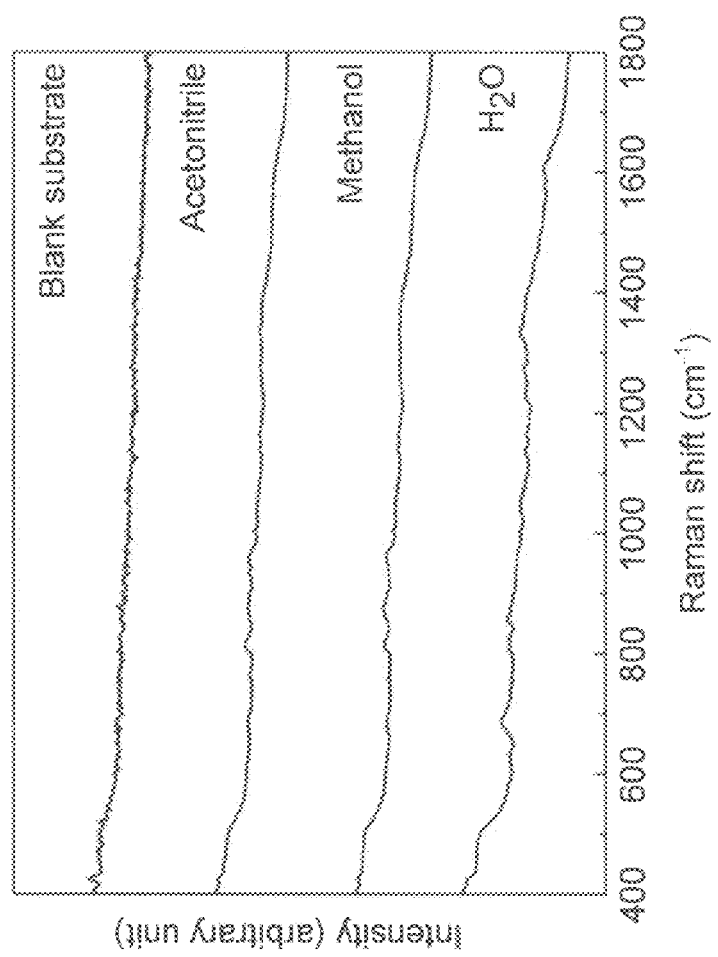
FIG. 2 is a graph that illustrates SERS spectra of various mobile phase solvents according to embodiments of the present disclosure.

SERS spectra of the solvents used in mobile phases were first collected (FIG. 2). After argon plasma cleaning, the blank substrates exhibited a low spectral background, where no significant peaks were found. Weak peaks at 690 $cm^{-1}$, 765 $cm^{-1}$, 810 $cm^{-1}$, 877 $cm^{-1}$, 958 $cm^{-1}$, and 1004 $cm^{-1}$ were found in the spectra of acetonitrile and methanol. Upon comparison with the spectra of other organic solvents (acetone, isopropanol, dichloromethane, and chloroform), it is suspected that the presence of the same spectral features shared by these peaks were a result of contaminant residues on the substrate surface, rather than from the solvents. In the spectrum of DI water, additional peaks at 855 $cm^{-1}$, 1051 $cm^{-1}$, 1136 $cm^{-1}$, 1229 $cm^{-1}$, 1275 $cm^{-1}$, 1330 $cm^{-1}$, 1607 $cm^{-1}$ were identified. Nonetheless, since the intensity of the background peaks was trivial compared to the analyte peaks, there was little or no interference to the analyte spectra after chromatogram development.

SERS of Single Components and Mixtures

Figure 3A:
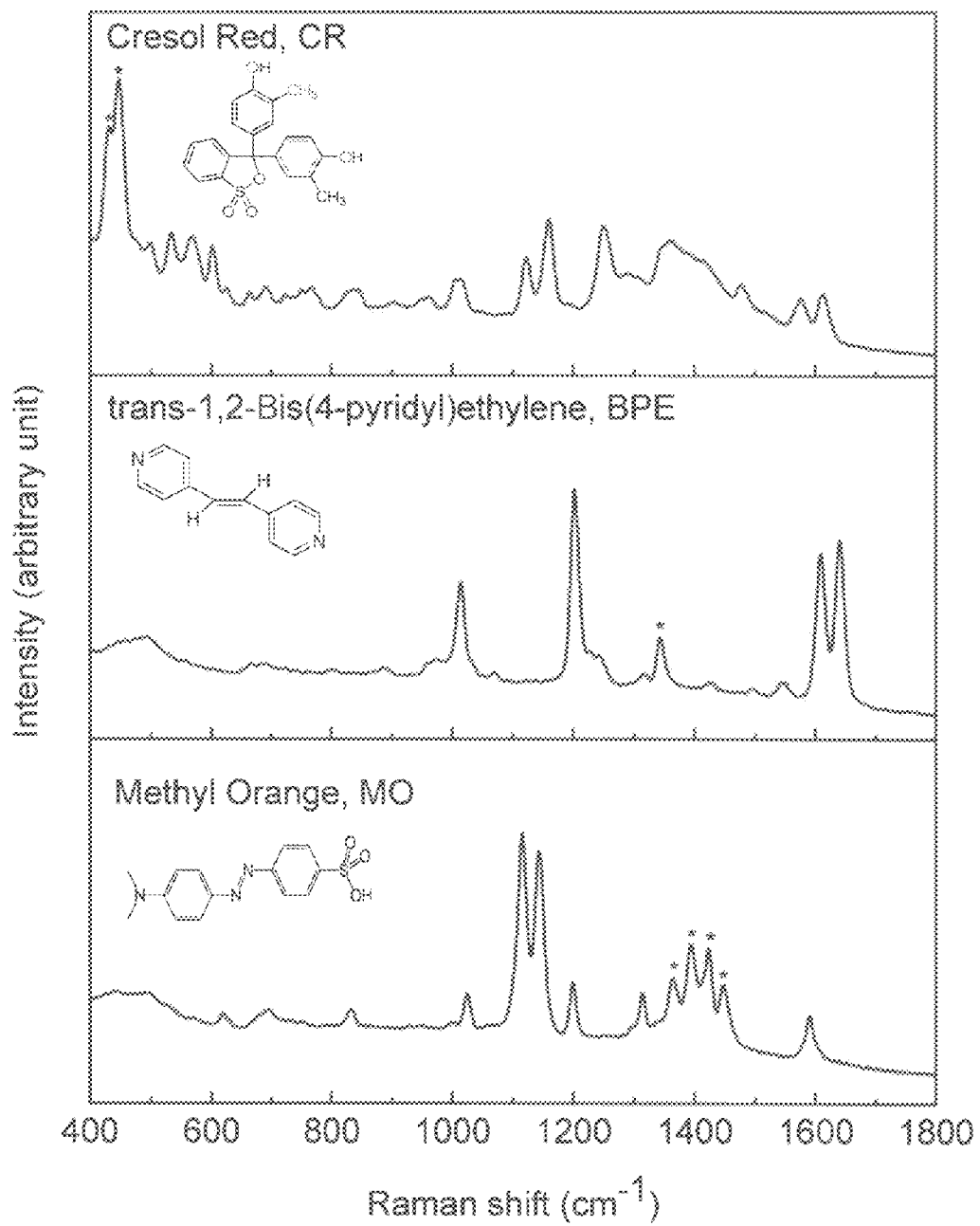
FIGS. 3A and 3B are graphs that illustrate SERS spectra of analytes in the three-component (a) and two-component (b) mixtures.
Figure 3B:
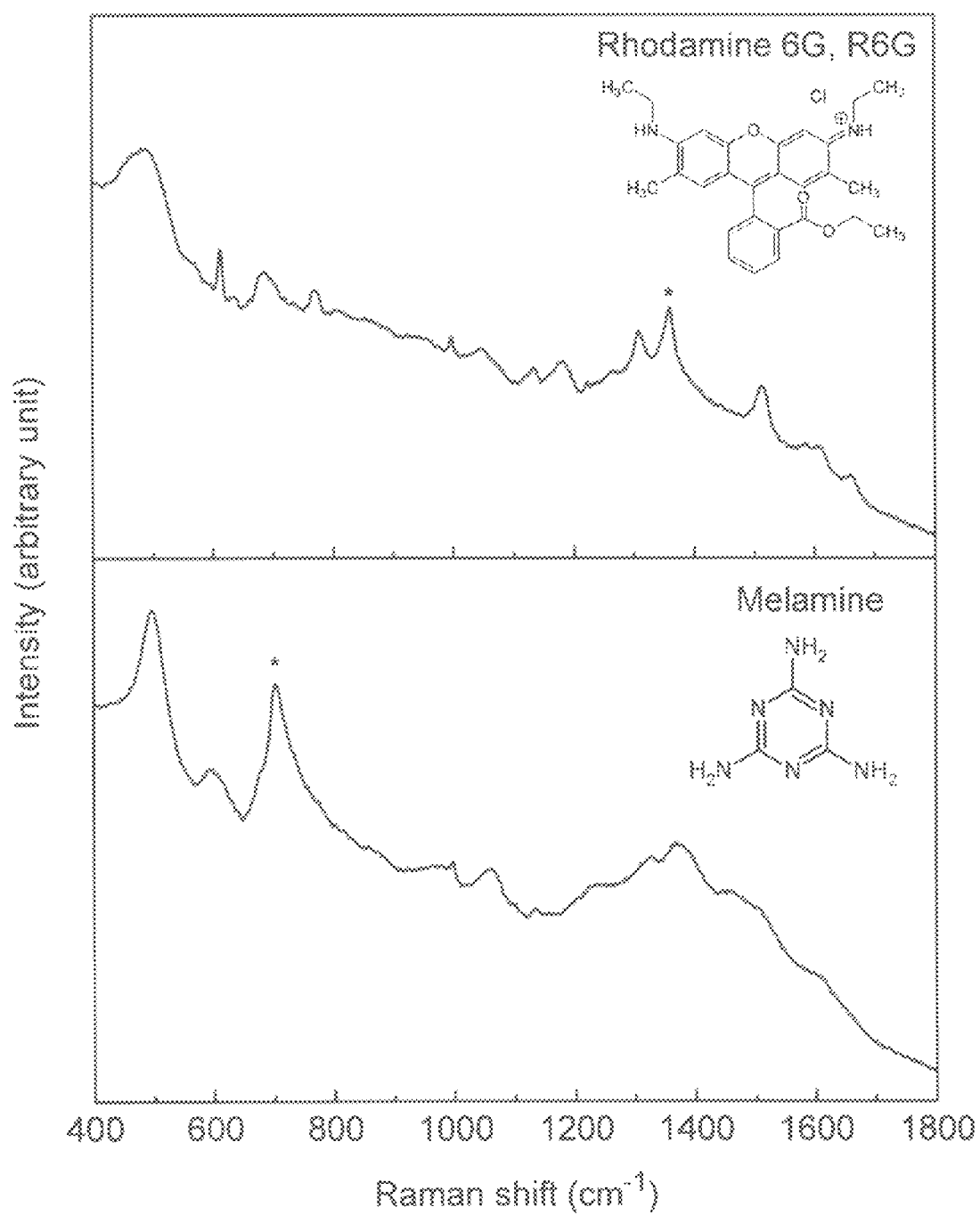

FIGS. 3(a) and 3(b) show the molecular structures of Cresol Red, BPE, Methyl Orange, melamine, and Rhodamine 6G, and the corresponding SERS spectra. Asterisks indicate the peak(s) chosen as representing peaks based on which peak intensity was estimated to generate the chromatogram for each component. Specifically, the 430-447 $cm^{-1}$ double peak, 1344 $cm^{-1}$ single peak, and the 1365-1447 $cm^{-1}$ quadruple peak were chosen for Cresol Red, BPE, and Methyl Orange, respectively, in the 3-component UTLC experiment. The peaks at 702 $cm^{-1}$ and 1360 $cm^{-1}$ were chosen as representatives of melamine and Rhodamine 6G, respectively.

UTLC Chromatogram

UTLC-SERS of Cresol Red, Methyl Orange, and BPE

Figure 4:
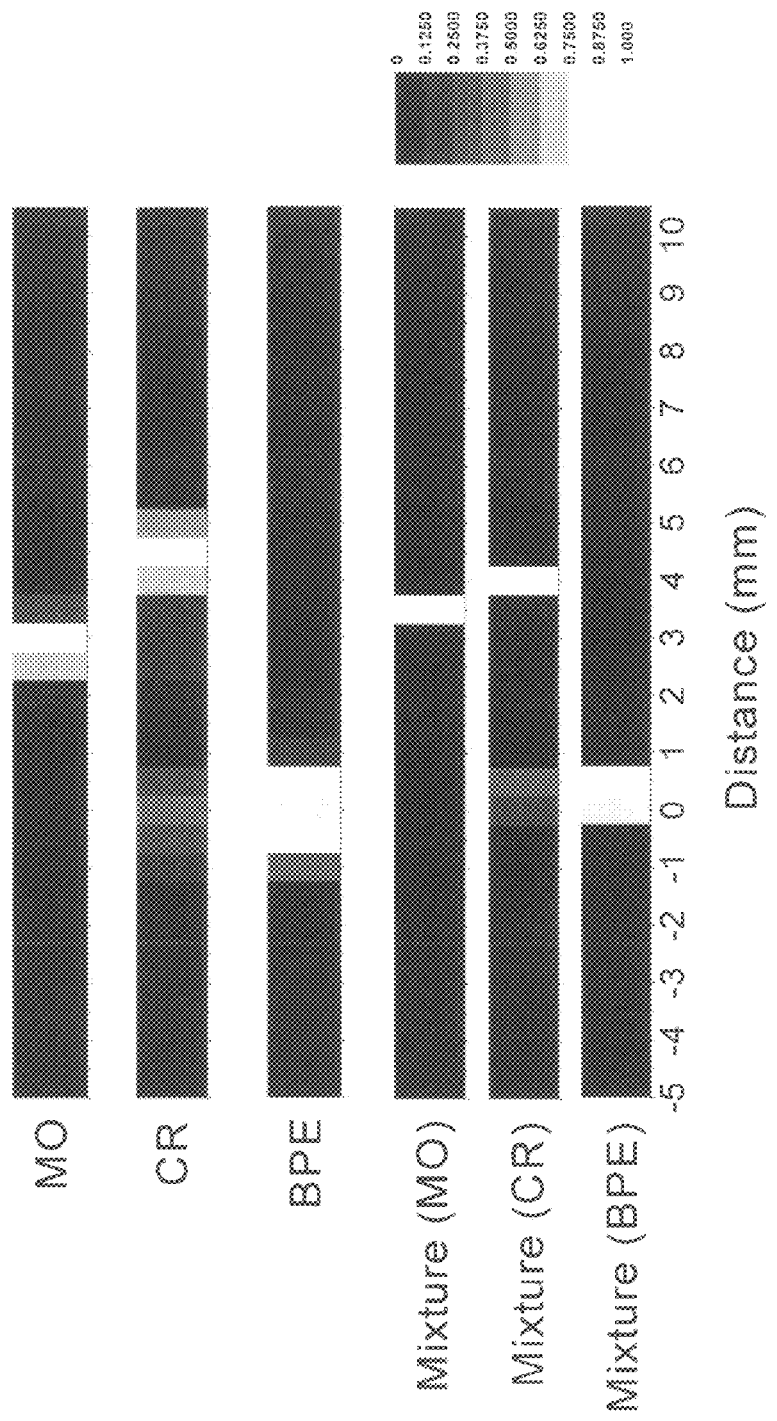
FIG. 4 illustrates separation of methylene orange (MO), cresol red (CR), and trans-1,2-Bis(4-pyridyl)ethylene (BPE) in an embodiment of the UTLC-SERS of the present disclosure.

As shown in FIG. 4, Methyl Orange, Cresol Red, and BPE were separable after a 5-min UTLC development. The solvent front travelled 8 mm from the sample origin, and the most intensive points for Methyl Orange, Cresol Red, and BPE in the mixture were 3.5 mm, 4 mm, and 0.5 mm, respectively. The migration distances for the corresponding pure analytes were 3 mm, 4.5 mm, and −0.5 mm, respectively. It is apparent that the $R_f$ values (0.44, 0.5, and 0.06) varied slightly in the mixture compared to the pure components (0.38, 0.56, and −0.06), possibly because mixing the analytes resulted in lower actual concentrations for each component, which is also manifested by the broader bands observed for the pure analytes. Nonetheless, due to the characterization capability of SERS, the components could not only be identified according to the $R_f$ values, but also be confirmed with SERS spectra simultaneously.

Figure 5:
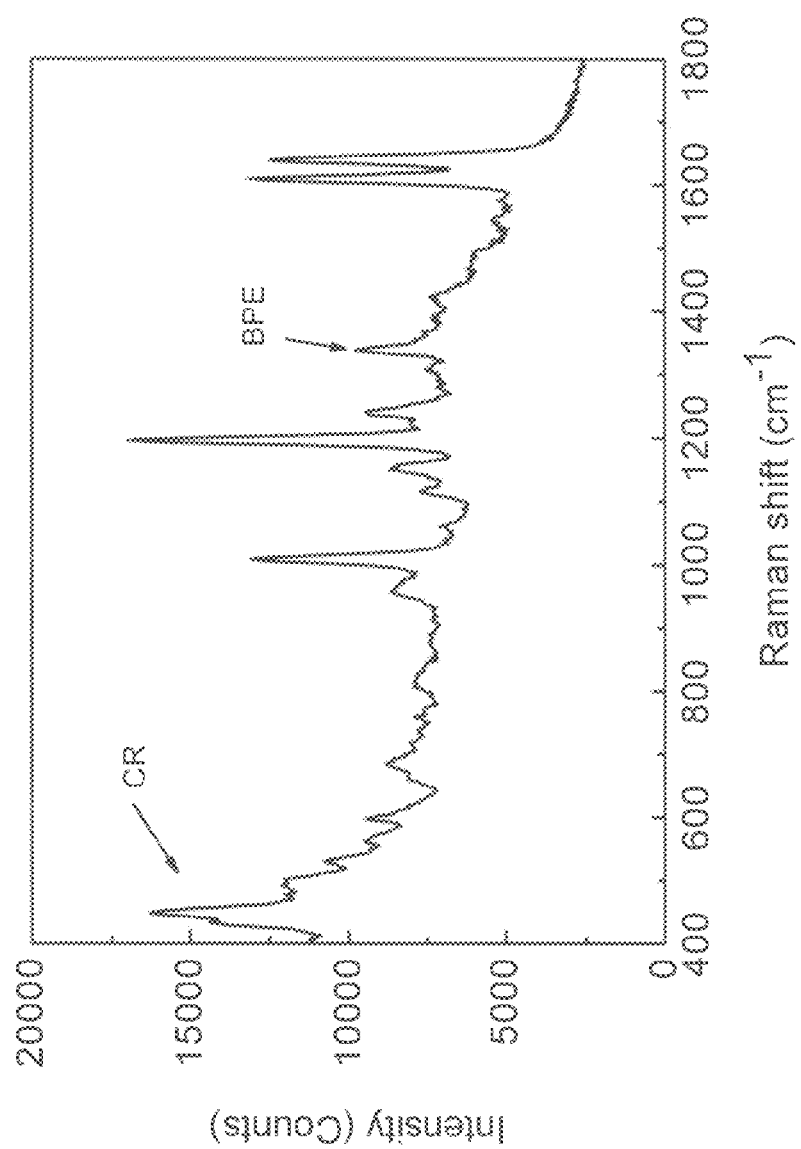
FIG. 5 is a graph that illustrates the Raman spectra of a mixture of CR and BPE near the sample origin according to an embodiment of the present disclosure.

Incomplete separation was observed for Cresol Red, in which one strong band appeared at $R_f$=0.5, and one weak band surrounding the sample origin. This would have caused confusion in conventional TLC which was solely based on $R_f$ readings, SERS detection was able to detect the presence of both components based on their unique spectral peaks (FIG. 5).

Limit of detection (LOD) for pure CR, MO, and BPE was assessed using each analyte serially diluted in DI water, both before and after UTLC development. The UTLC process did not affect the LODs.

TABLE 1

Limit of Detection:

| | LOD (ng/UTLC spot) | | LOD (pg/laser spot) | |
|---|---|---|---|---|
| Analyte | Before UTLC | After UTLC | Before UTLC | After UTLC |
| CR | 0.404 | 0.404 | 4.0441 | 4.0441 |
| BPE | 0.0182 | 0.0182 | 0.1822 | 0.1822 |
| Mo | 3.27 | 0.327 | 32.733 | 3.2733 |

UTLC of Melamine and Rhodamine 6G

Figures 6A, 6B:
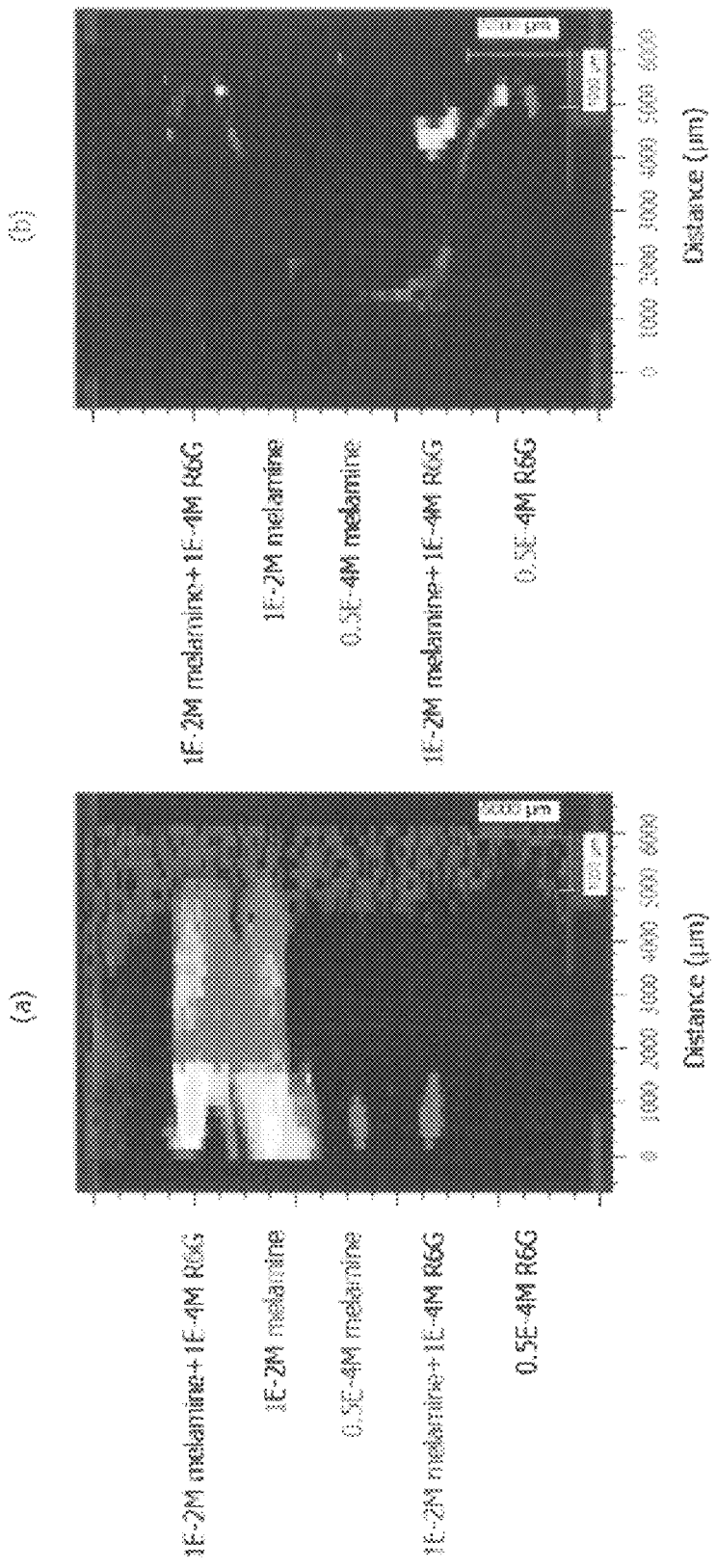
FIGS. 6A-6B illustrate mapping peak intensities of melamine and R6G, (a) melamine 600 cm$^{-1}$ peak intensity, (b) R6G 610 cm$^{-1}$ peak intensity.

Since Rhodamine 6G has significantly higher solubility in methanol (400 g/L) than melamine (<1 g/L), it was easy for the two to be separated in methanol. Not surprisingly, the mixture of $1\times10^{-2}$ M melamine and $1\times10^{-4}$ M Rhodamine 6G exhibited only the melamine spectrum before UTLC, as more melamine molecules tend to outcompete the Rhodamine 6G molecules for binding sites on the silver surface. After UTLC, the Rhodamine 6G molecules were carried with the solvent to the front of migration, where less, if any competition occurred, resulting in a visibly concentrated zone of Rhodamine 6G. SERS spectra also confirmed the presence of this zone. At sample origin, because of the extremely high concentration used, melamine molecules were likely to have formed multilayers, where only a small portion of melamine molecules were efficiently bound to the AgNR surface, and the rest reside on top of the bottom layer of bound molecules, instead of being adsorbed onto the silver surface through chemical bonding or physical contact. During UTLC, these excess melamine molecules were carried over by the migrating solvent flow, and became adsorbed onto the free binding sites of the AgNRs along the migration direction, forming undesired tailing in the reverse direction (FIG. 6a). In contrast, as the concentration decreased to $0.5\times10^{-4}$ M, melamine molecules became more confined to the sample origin, as fewer molecules were more likely to form a single layer on the AgNR surface, and the number of unbound molecules decreased significantly as well.

In this study the 610 $cm^{-1}$ and 600 $cm^{-1}$ peaks were used as indicative peaks for Rhodamine 6G and melamine, respectively. The 610 $cm^{-1}$ peak, instead of the 1360 $cm^{-1}$ peak, was chosen for Rhodamine 6G mainly because the Renishaw Raman System allowed the mapping result to be generated within a shorter period of time if the scattered light was collected within a close range of wavenumbers (e.g., between 400 $cm^{-1}$ to 800 $cm^{-1}$) than in the full-spectrum range. High-resolution mapping was employed in this study to monitor the migration of molecules at different concentrations. In FIG. 6(a), it is obvious that at concentrations as high as $10^{-2}$ M, 0.1 μL of melamine was able to spread into the adjacent lanes and confounding the interpretation of the chromatogram. On the other hand, the distribution of Rhodamine 6G intensities were largely affected by the pathways of the mobile phase solvent, as the molecules travelled along with methanol at the very front of migration. As the migration distance increases, the width of R6G bands also tended to slightly increase. It was possible for molecules belonging to different lanes to mingle with one another, especially when crooked solvent front appeared, though it was very rare. Therefore, it is necessary to introduce artificial barriers against cross-contamination during UTLC development. One means to tackle this issue is to pattern the UTLC-SERS plate into multiple channels so that each sample is confined within its own channel.

REFERENCES

1. S. B. Chaney, S. Shanmukh, R. A. Dluhy and Y. P. Zhao, *Appl Phys Lett,* 2005, 87.
2. H. Chu, Y. Huang and Y. Zhao, *Applied spectroscopy,* 2008, 62, 922-931.
3. P. Negri, N. E. Marotta, L. A. Bottomley and R. A. Dluhy, *Applied spectroscopy,* 2011, 65, 66-74.

Example 2

Methods

Standard 1×3 inch glass substrates were prepared for the thin layer chromatography (TLC) experiment: 20 nm Ti+200 nm Ag film+2000 nm AgNR (87)°.

Figure 7:
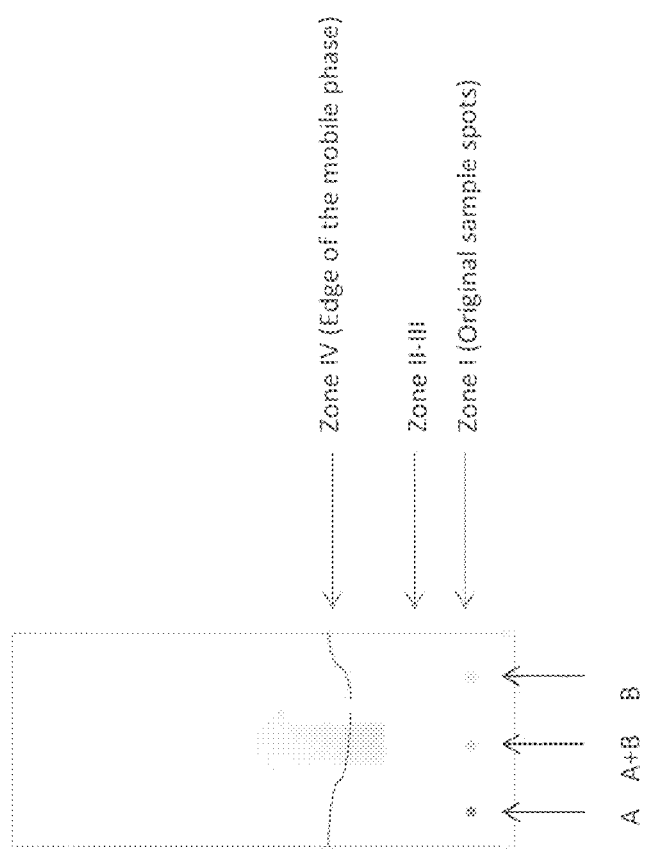
FIG. 7 illustrates an embodiment of the UTLC-SERS chip set up of the present disclosure.

TLC conditions included the following: Spot ~0.1 μL sample solutions on the substrate, about 1 cm away from the short edge (FIG. 7), and let dry. Meanwhile, mix the mobile phase solvents in a glass beaker and cover with a petri dish lid to saturate the TLC chamber. Put the substrate in the beaker; make sure the sample spots are above the solvent surface. Cover the beaker with petri dish lid, and then let TLC develop until the mobile phase stops moving upward. Take the substrate out and very gently dry the residue solvents with $N_2$.

SERS measurements: Starting from the original sample spots (visible on the substrate), move the laser point about 2-3 mm further away from the original spots towards the direction of TLC development.

Experiment I

Mobile phase=IPA:CHCl3:H2O=3:1:1

Sample: Melamine (1 mM), R6G ($10^{-4}$ M), and their 1:1 mixture.

Figure 8:
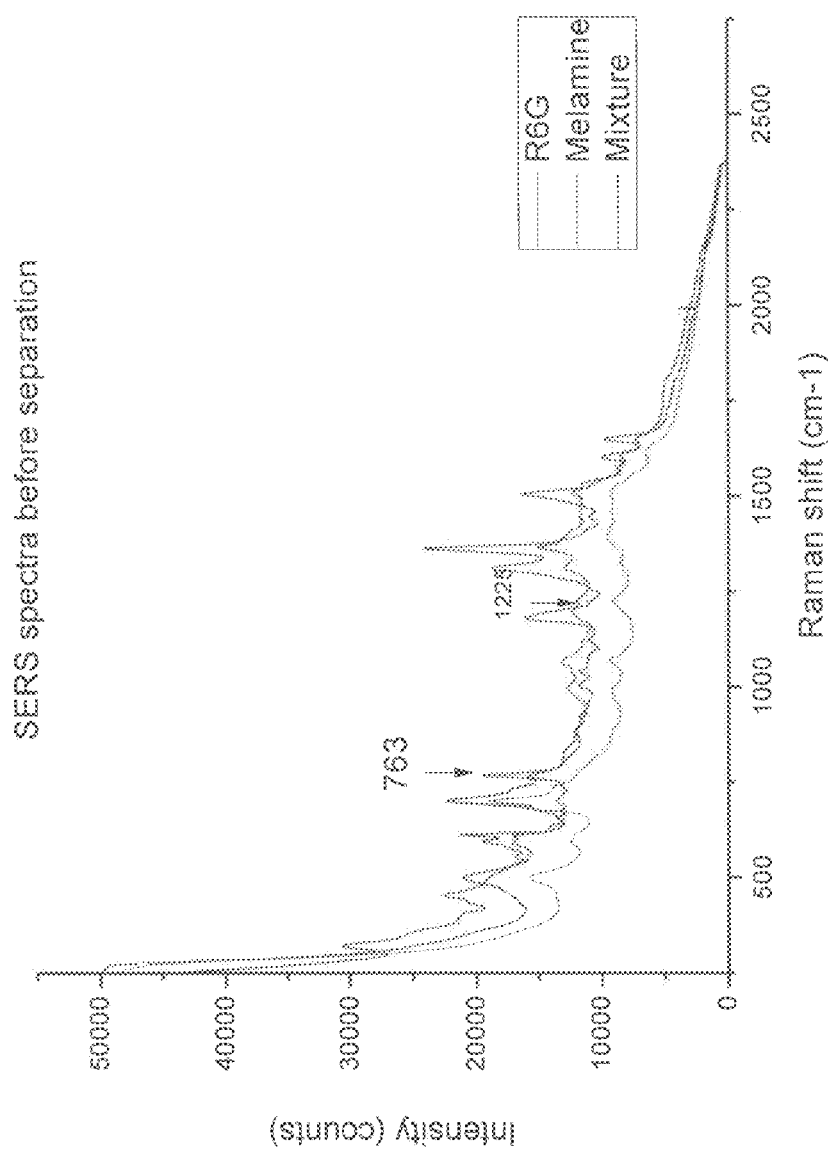
FIG. 8 is a graph that illustrates SERS spectra before UTLC separation according to an embodiment of the present disclosure.

FIG. 8 illustrates the SERS spectra before separation. Major peaks for each sample (the peaks in the mixture sample are marked with bold and underline, representative of melamine and R6G contribution):

Melamine: 500, 592-610, 699, 733, 993, 1068, 1223, 1325, 1392, 1612

R6G: 451, 595, 610, 763, 1003, 1035, 1178, 1310, 1360, 1504, 1443, 1506, 1573, 1600, 1647

Mixture: 500, 594, 612, 701, 996, 1065, 1193, 1310, 1362, 1504, 1600, 1647

After separation:

| Zone | Melamine | R6G | Mixture |
|---|---|---|---|
| I | Max: 595-608, 701, 1070, 1225, 1327, 1384, 1518 | Max: 490, 594, 683, 763, 805, 924, 998, 1045, 1179, 1313, 1360, 1496, 1600, 1650, 1773 | Max: 502, 609, 706, 1070, 1223, 1392, 1506, |
| II | 488, 686, 805, 1043, 1776 | | Max: 488, 592, 686, 763, 807, 1045, 1176, 1305, 1362, 1490, 1606, 1650, 1772 |
| III | | | |
| IV | | | |

Background (IPA:CHCl$_3$:H$_2$O=3:1:1): 488, 688, 956, 1052, 1772(w)

Clearly, after separation, melamine stayed close to its original position (it moved very slowly or hardly moved along with the mobile phase and settled at Zone I), whereas R6G traveled faster and eventually settled near the front edge of the mobile phase (Zone III). But in the R6G spectra there were also contamination peaks from the mobile phase, which also moved fast. In summary, the separation was able to separate melamine from faster moving molecules such as R6G and contaminants in the solvent (whatever they are), but R6G could not be separated from the contaminants.

Figure 9:
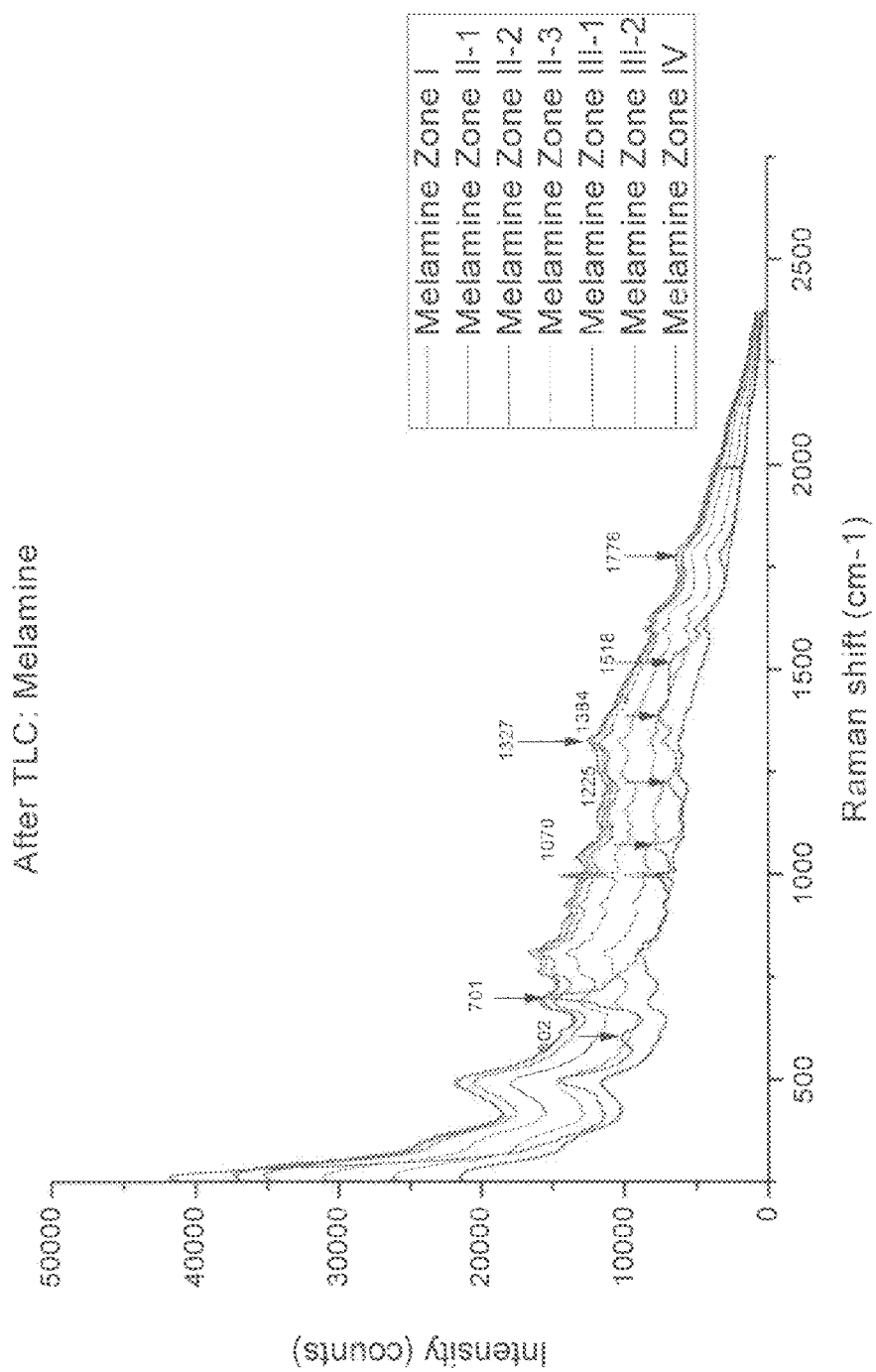
FIG. 9 is a graph that illustrates SERS spectra of melamine after UTLC separation according to an embodiment of the present disclosure.
Figure 10:
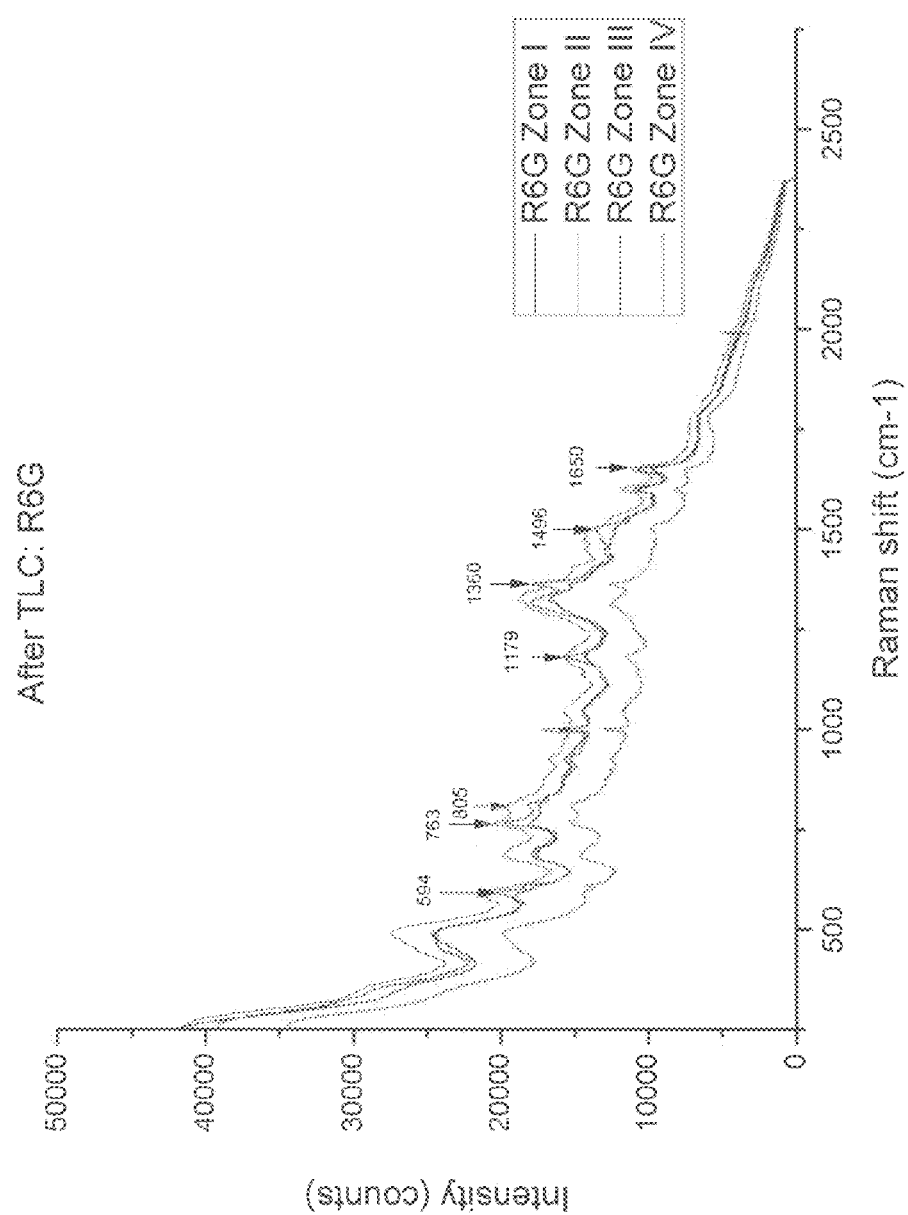
FIG. 10 is a graph that illustrates SERS spectra of R6G after UTLC separation according to an embodiment of the present disclosure.
Figure 11:
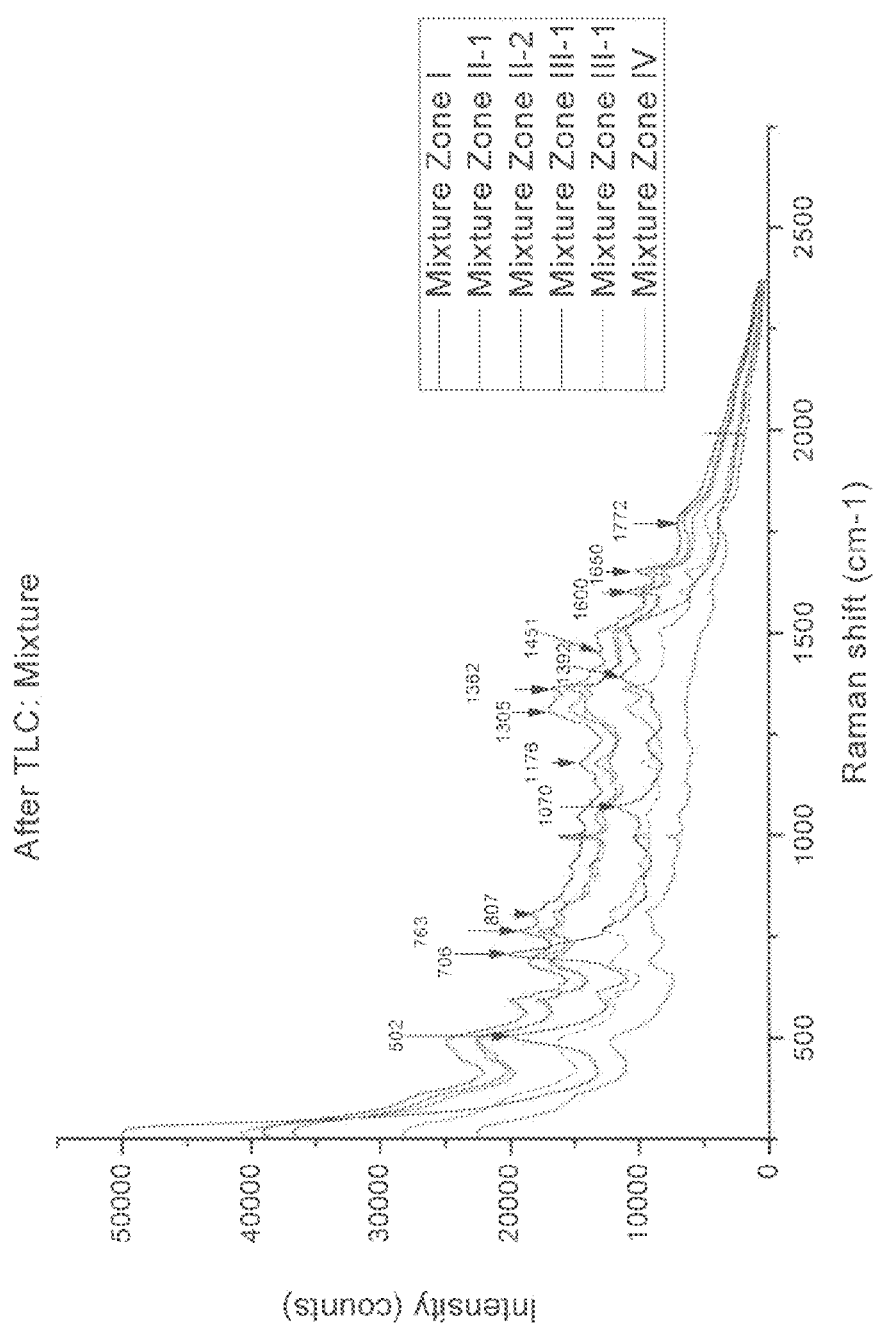
FIG. 11 is a graph that illustrates SERS spectra of a mixture after UTLC separation according to an embodiment of the present disclosure.
Figure 12:
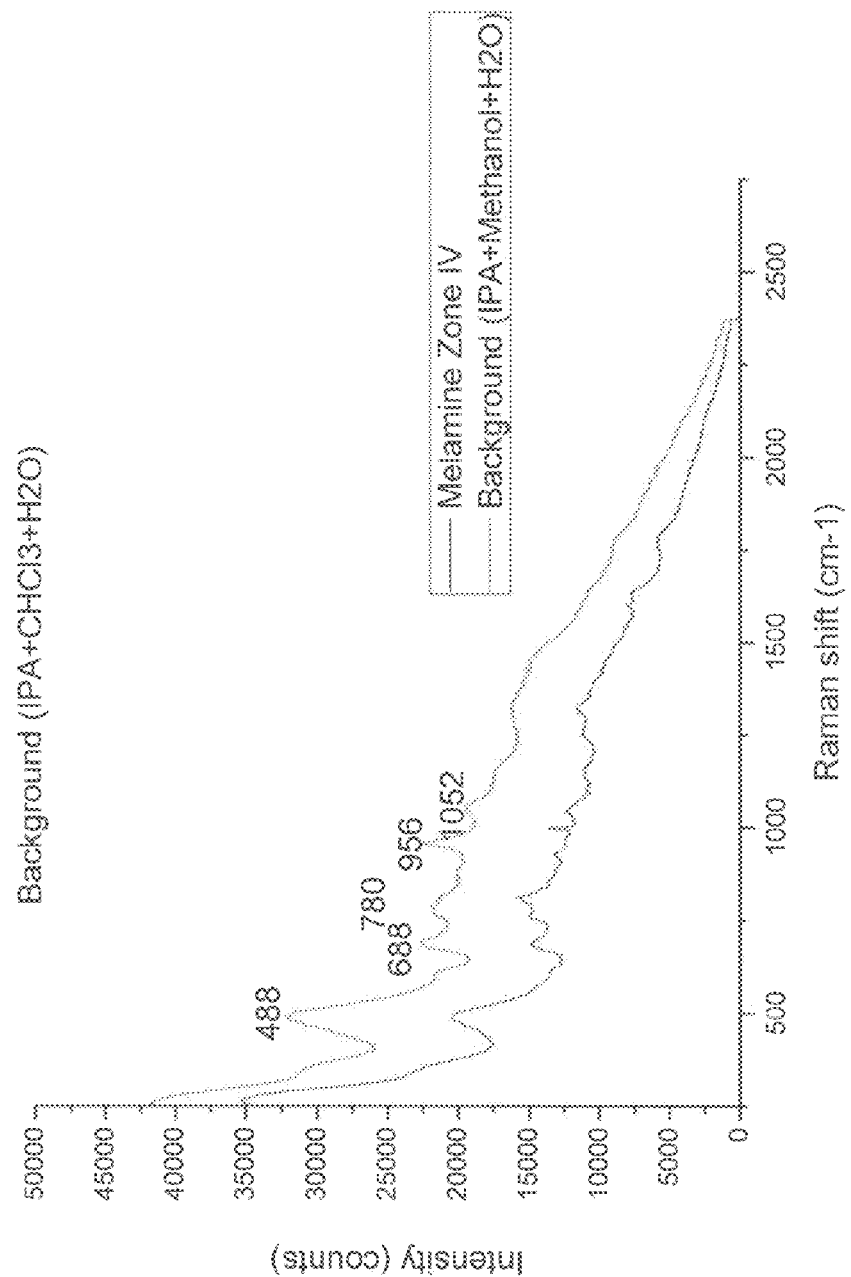
FIG. 12 is a graph that illustrates background SERS spectra according to an embodiment of the present disclosure.
Figure 13:
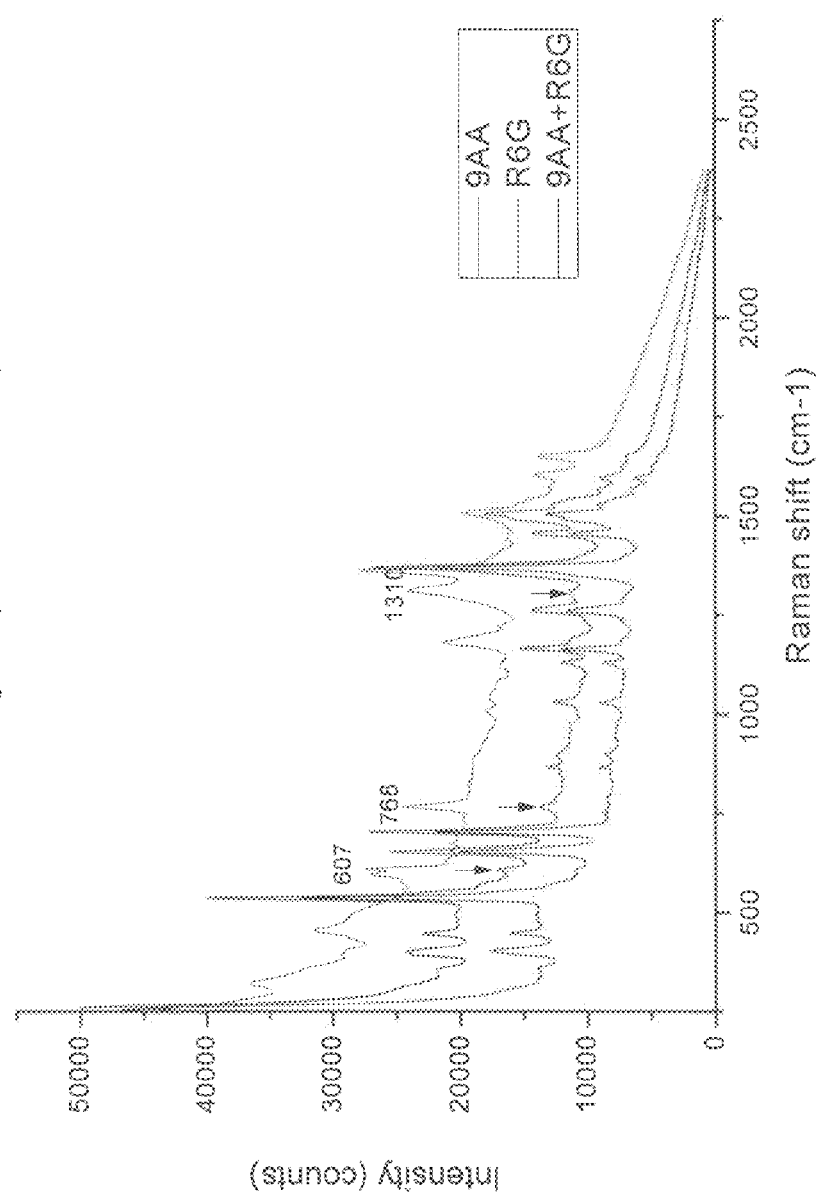
FIG. 13 is a graph that illustrates averaged spectra of two reporters and their mixture before UTLC according to an embodiment of the present disclosure.
Figure 14:
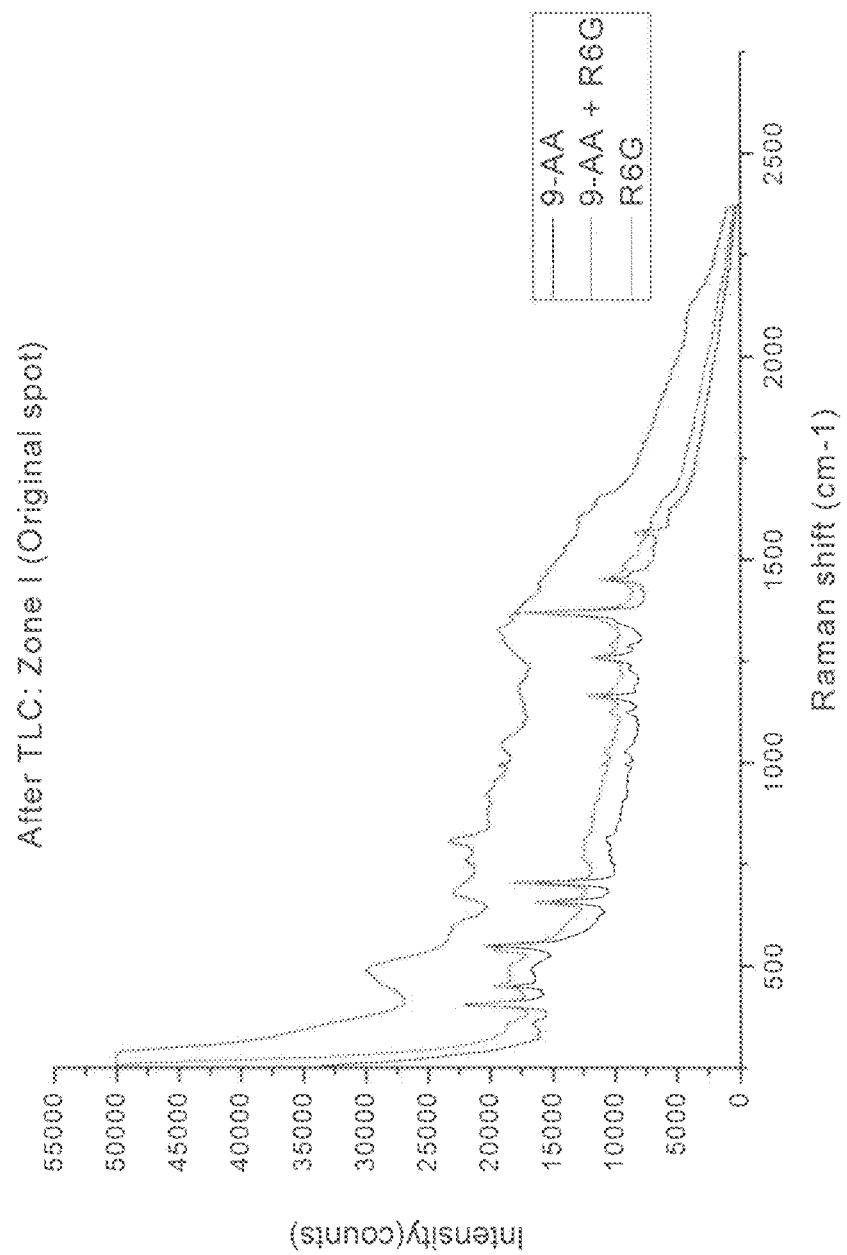
FIG. 14 is a graph that illustrates Raman spectra at the sample origin according to an embodiment of the present disclosure.
Figure 15:
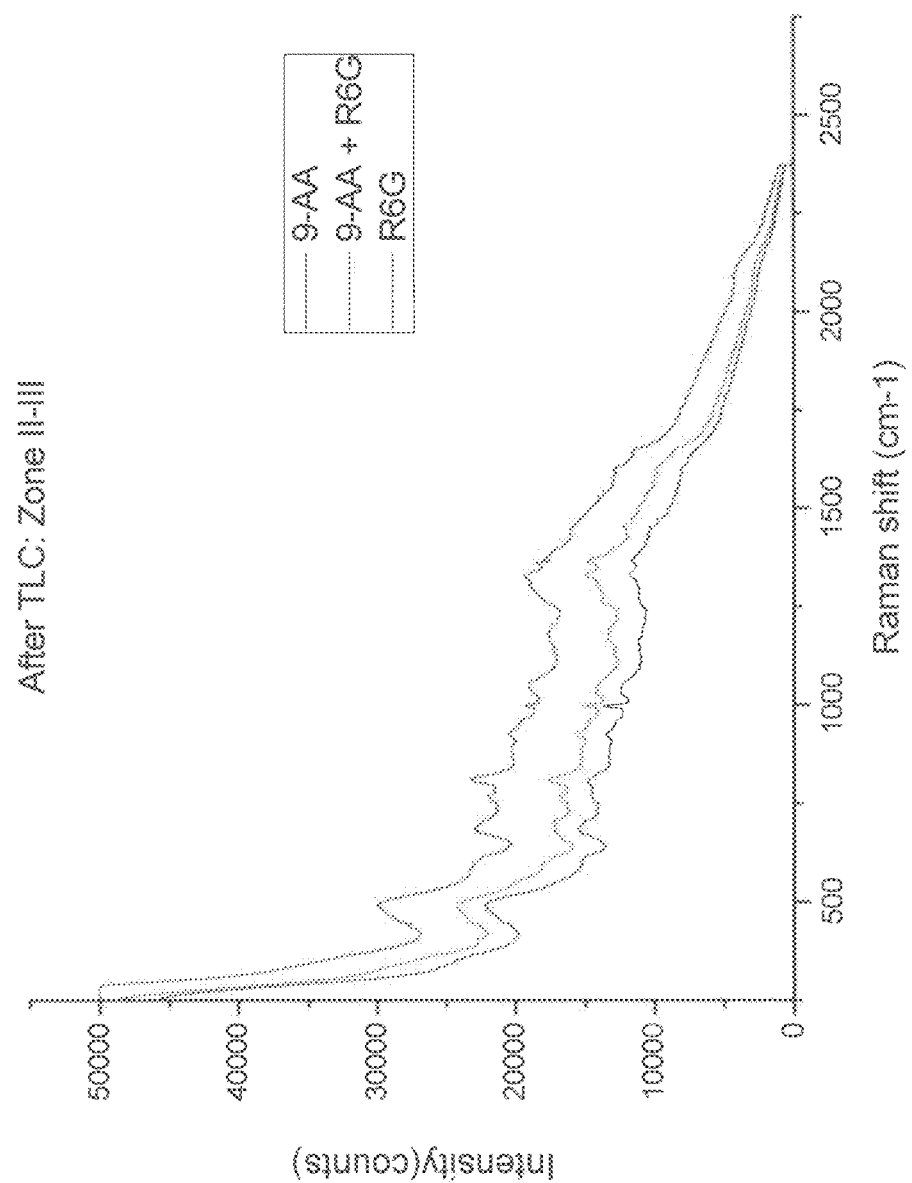
FIG. 15 is a graph that illustrates Raman spectra obtained along the development direction according to an embodiment of the present disclosure.
Figure 16:
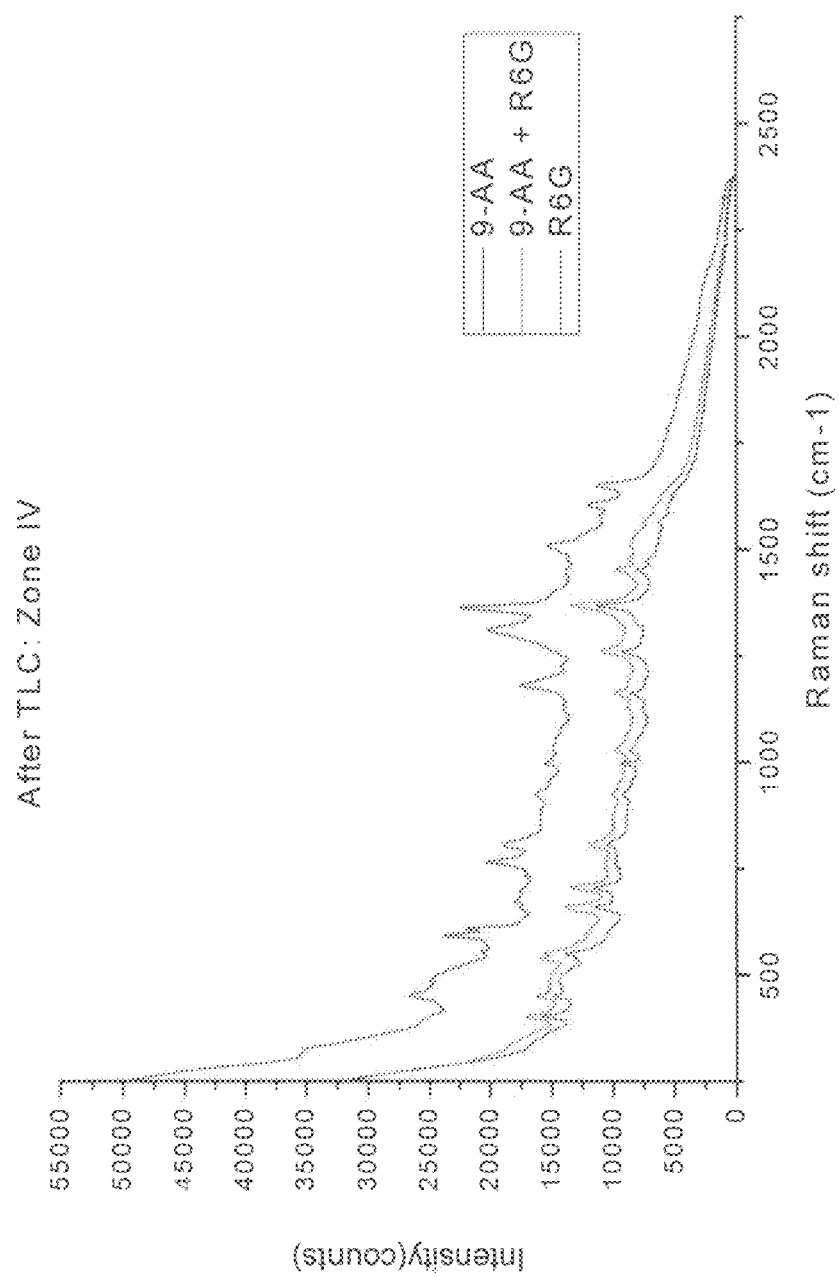
FIG. 16 is a graph that illustrates Raman spectra at the edge of the mobile phase according to an embodiment of the present disclosure.
Figures 17A, 17B:
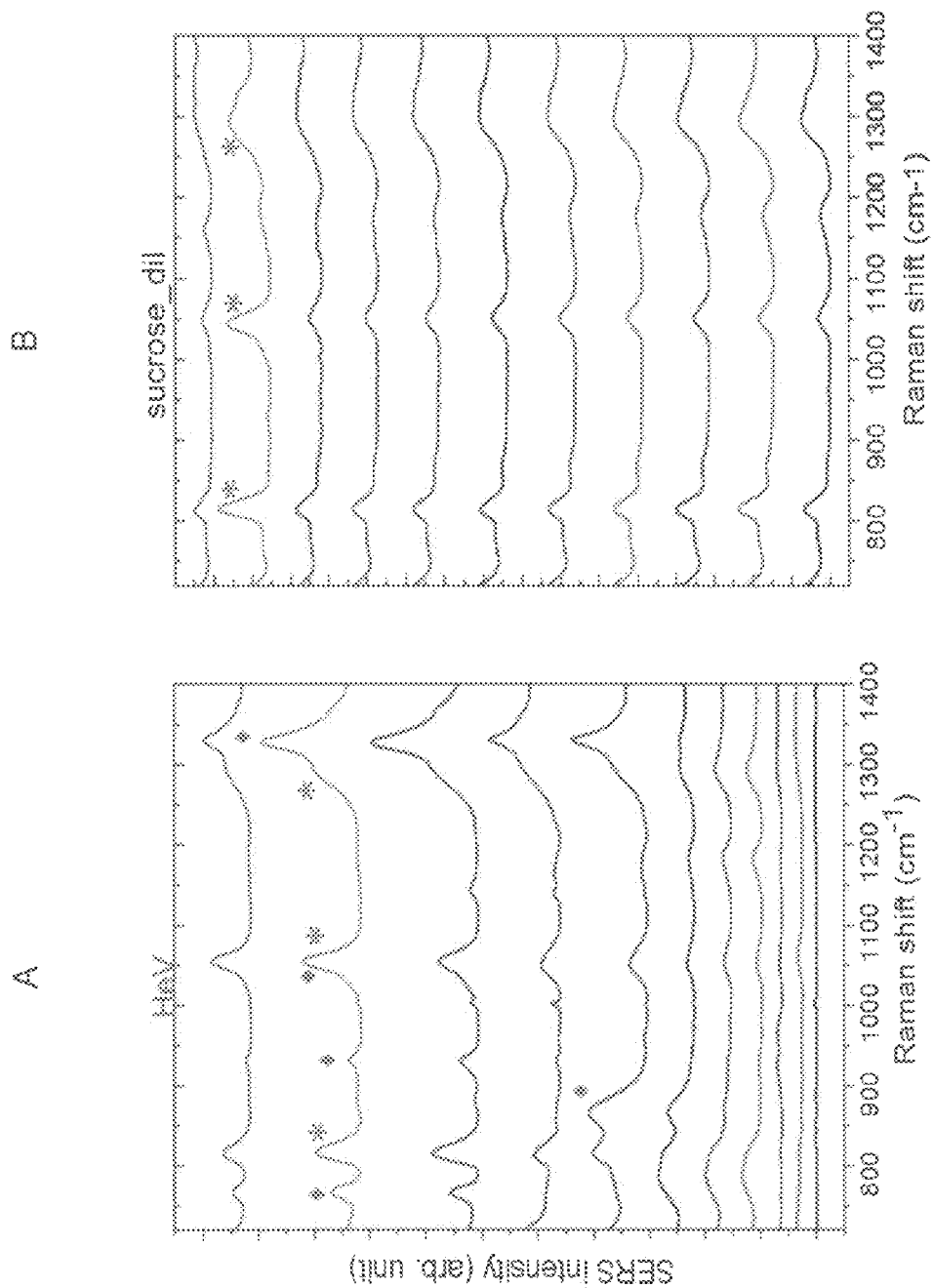
Figures 18A, 18B, 18C:
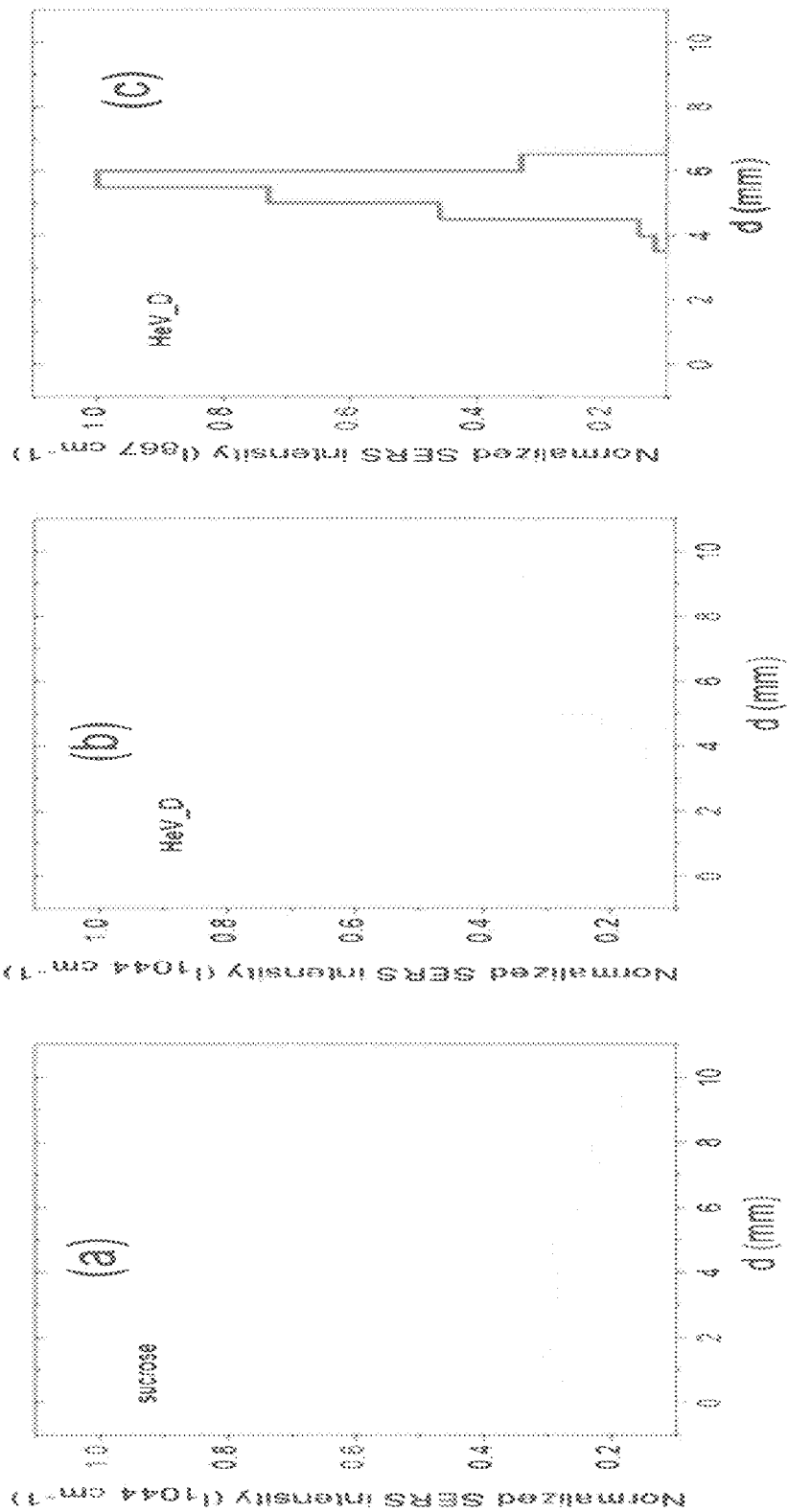
FIGS. 18A-18C are graphs that illustrate normalized SERS intensity of characteristics peak of sucrose at 1044 cm-1 plotted as a function of distance d from the droplet center (d=0) for (a) sucrose ($10^6$ fold diluted in 18 MΩ water) and (b) dialysis HeV. The HeV virus was dialysis in 18 MΩ water that diluted the amount of sucrose in virus solution by a factor of $10^6$. (c) The characteristic peak at 867 cm-1 for HeV virus as a function of distance d.
Figures 19A, 19B, 19C:
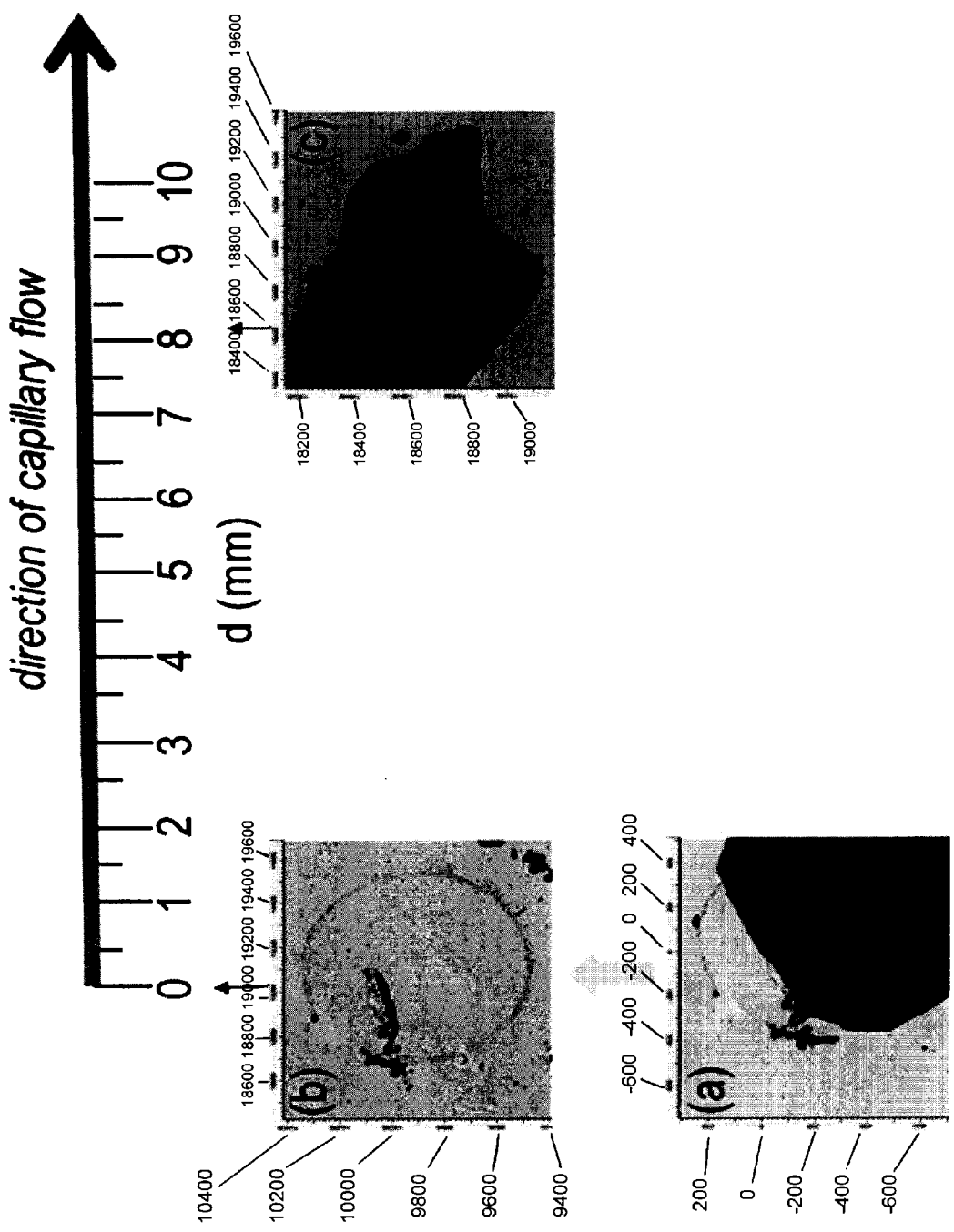
FIGS. 19A-19C illustrate (a) Sucrose droplet deposited on the AgNR SERS substrate, (b) sucrose moved away from the original spot to (c) an about 8 mm after the TLC measurements.
Figures 20A, 20B, 20C:
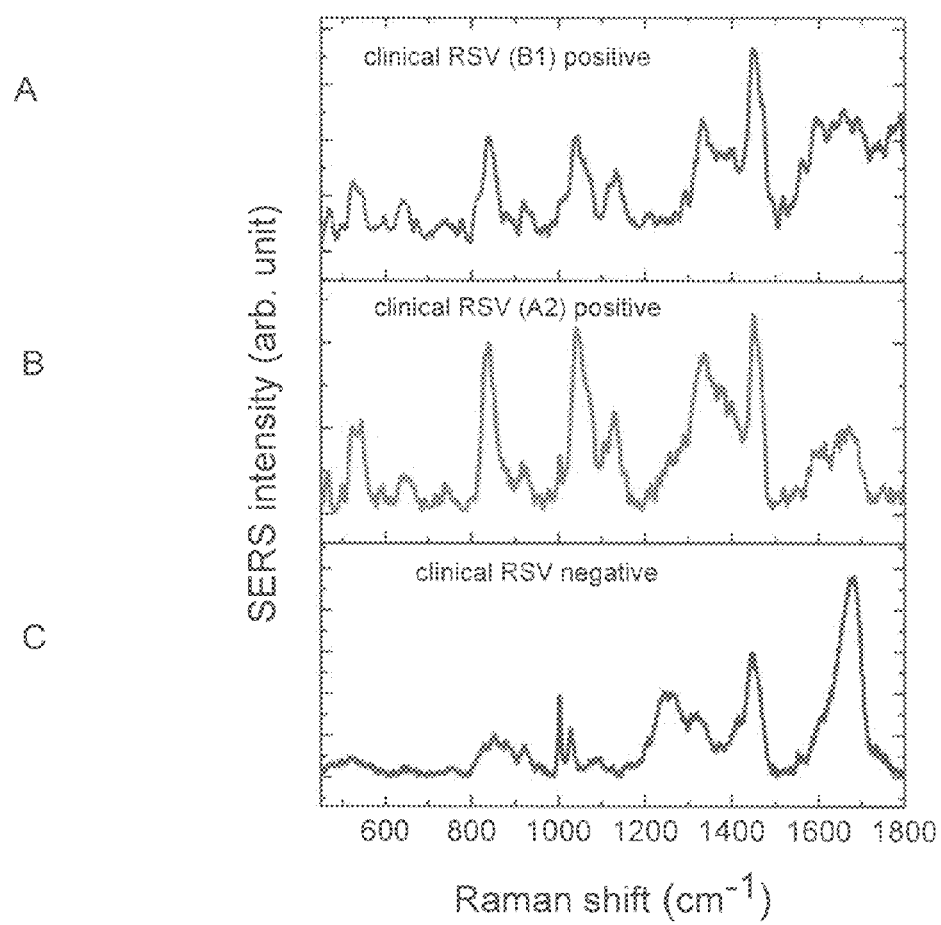
FIGS. 20A-20C are graphs that illustrate SERS spectra of clinical RSV (strain B1)-positive samples (a); clinical RSV (strain A2)-positive samples (b); and RSV-negative clinical background (c).
Figures 21A, 21B, 21C:
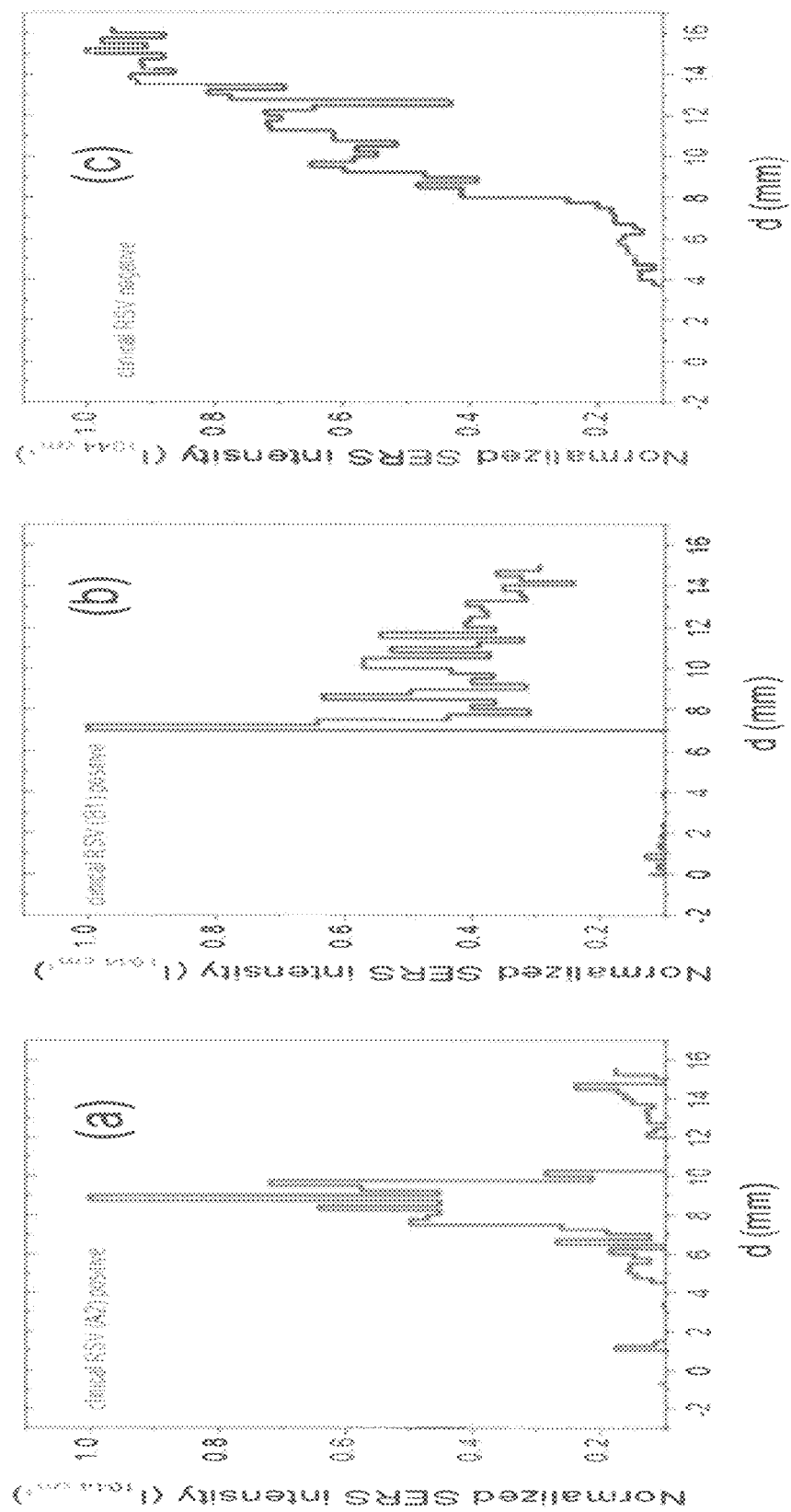
FIGS. 21A-21C are graphs that illustrate normalized SERS intensity of major characteristics peak of RSV at 1044 cm-1 plotted as a function of distance d from the droplet edge for (a) clinical RSV (A2) positive, (b) clinical RSV (B2) positive, and (c) clinical RSV negative.

There was no contamination peaks at Zone I of melamine and mixture samples, but they existed at Zone I of R6G sample. It is possible that the solvent itself generates some SERS signal that was masked by the presence of melamine. The corresponding spectra are illustrated in FIG. 9.

Experiment II

Mobile phase: toluene: methanol=1:1
Samples: 9-AA (1 mM), R6G ($10^{-4}$ M), and their 1:1 mixture.

Before separation, the spectra for 9-AA and R6G were clearly distinguishable, but their mixture resembled 9-AA very much. Only three peaks at 607, 768, and 1310 from the R6G spectrum were also shown at the mixture spectrum.

After separation, R6G travelled to the front edge of the mobile phase—the featured spectra were only seen in Zone IV (farthest from the original spot); 9-AA spectra were seen at both Zone I and Zone IV, but not the area in between. For the mixture sample, its 9-AA component behaved exactly as the 9-AA sample, but the R6G component was nowhere to find in all of the zones in the development direction.

9-AA and R6G were chosen for the first experiment because they are both fluorescent dyes, but under UV lamp, it was impossible to even locate the original sample spots, probably due to the very small volume used. They are probably not good examples in this experiment because the spectrum of their mixture is very hard to be differentiated from the 9-AA spectrum, or the volume ration needs to be adjusted so that one does not dominate the other.

Example 3

Thin Layer Chromatography Measurements

Samples: (1) HeV/NiV+sucrose as received samples were dialysis using 18 MΩ water. The dialysis process dilutes the sucrose concentration by a factor of $10^6$. (2) Clinical RSV (A2 and B1) positive and clinical RSV negative.

A 1×1 inch$^2$ Ag nanorod arrays SERS substrate was used. The substrate was plasma cleaned in argon 30 W for 2 minutes. 0.1 µL droplets of samples were deposited on the AgNR substrate about 5 mm apart from the sample edge. The droplets were aligned with the marked line at the edges. The SERS measurements were performed on the droplets after they are dry (about 5 mins).

Then, the spotted SERS substrate was put in the beaker such that spots are just above the methanol liquid surface for about 5 mins. The SERS substrate was taken out slowly without disturbing the liquid, let it dry in the hood for about 2 mins.

SERS measurements were performed by using a 5×20 to 60 (x×y) rectangular SERS measurement grid for each droplet spots having Δx=80 µm and Δy=0.5 mm (sucrose and HeVD) and 0.25 mm (for RSV samples). See FIGS. 17-21 for further illustration with regard to Example 3.

TABLE 1

SERS peaks from dialysis HeV and sucrose_dil spectra and their possible assignments.

| Assignment | HeV virus [SERS shifts (cm-1)] | Sucrose_dil [SERS shifts (cm-1)] |
|---|---|---|
| Trptophan | 766 | 815 |
| Trptophan | 867 | |
| C=C deformation, Trptophan | 930 | |
| Phenylalanine | 1002 | 1044 |
| ribose | 1055 | |
| Amide | 1290 | 1290 |
| CH deformation, Adenine | 1330 | |

TABLE 2

SERS peaks from RSV in clinical background spectra and their possible assignments.

| Assignment | RSV [SERS shifts (cm-1)] |
|---|---|
| Disulfide stretching | 527, 546 |
| Tyr | 837-840 |
| C—N stretching | 1044 |
| CH2 deformation | 1456 |

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In an embodiment, the term "about" can include traditional rounding according to the numerical value. In addition, the phrase "about 'x' to 'y'" includes "about 'x' to about 'y'".

It should be emphasized that the above-described embodiments of the present disclosure are merely possible examples of implementations, and are merely set forth for a clear understanding of the principles of the disclosure. Many variations and modifications may be made to the above-described Therefore, at least the following is claimed:

1. A method of simultaneous analyte separation and detection in a sample, comprising:
   providing a SERS-active UTLC chip, wherein the SERS-active UTLC chip comprises an array of nanostructures on a surface of a substrate;
   applying at least one sample comprising at least one analyte to the SERS-active UTLC chip;
   acquiring at least one SERS spectra for each sample at a sample origin on the chip;
   immersing at least a portion of the SERS-active UTLC chip in a mobile phase solvent, wherein the at least one sample is above the mobile phase solvent;
   developing the chip so that the at least one analyte is physically separated;
   acquiring at least one SERS spectra for each sample along an UTLC development direction; and
   analyzing all of the SERS spectra to identify the at least one analyte in each sample.

2. The method of claim 1, wherein the array of nanostructures comprise Ag nanorods fabricated by oblique angle deposition (OAD).

3. The method of claim 2, wherein a tilt angle β between an individual nanorod and the substrate surface is less than about 90 degrees.

4. The method of claim 3, wherein the OAD fabrication comprises:
   rotating the substrate in a polar direction relative to a vapor arrival line of a vapor flux of a material to achieve a desired incident angle between the vapor arrival line and the substrate;
   optionally rotating the substrate azimuthally;
   exposing at least a portion of the surface of the substrate to the vapor flux of a material at the desired incident angle; and
   forming the array of nanorods on the surface of the substrate.

5. The method of claim 4, wherein the substrate is planar, wherein an incident angle φ is defined by the vapor arrival line and the surface normal of the planar substrate, and wherein φ is greater than about 75°.

6. The method of claim 4, wherein the vapor flux of material includes a material selected from the group consisting of: a metal, a metal oxide, a metal nitride, a metal oxynitride, a polymer, a multicomponent material, and a combination thereof.

7. The method of claim 6, wherein the material is selected from the group consisting of: silver, nickel, aluminum, silicon, gold, platinum, palladium, titanium, cobalt, copper, zinc, oxides of each, nitrides of each, oxynitrides of each, and a combination thereof.

8. The method of claim 4, further comprising disposing one or more substantially uniform layers of a material on a portion of the substrate surface and forming the array of nanorods on the uniform layer.

9. The method of claim 8, wherein the material is selected from: a metal, a metal oxide, a metal nitride, a metal oxynitride, a polymer, a multicomponent material, and a combination thereof.

10. The method of claim 1, wherein the sample is selected from the group consisting of: a buccal cell, a buffered solution, saliva, sweat, tear, phlegm, urine, blood, plasma, serum, breath condensate, cerebrospinal fluid, lymph, a cell, a microorganism, a wash from vegetables, a wash from fruits, a polluted water sample, a meat sample, a combination thereof, and an aqueous dilution thereof.

11. The method of claim 1, wherein the analyte is selected from the group consisting of: melamine, a contaminant, a biomarker, a polypeptide, a protein, a glycoprotein, a nucleic acid, a eukaryotic cell, a prokaryotic cell, a virus, a bacterium, a protozoa, a apicomplexan, a trematodes, a nematodes, a fungus, a spore, a carbohydrate, a lipid, a vitamin, a mycrotoxin, a drug, a pesticide, and a combination thereof.

12. The method of claim 1, wherein the analyte comprises at least one compound within a mixture.

13. The method of claim 1, wherein the SERS-active UTLC chip is patterned with at least one channel so that each of the at least one sample is applied in its own channel to avoid cross contamination.

14. The method of claim 1, wherein the mobile phase solvent is selected from the group consisting of: methanol, acetonitrile, hexane, hexanol, ethanol, propanol, isopropanol, chloroform, dichloromethane, acetone, ethyl ether, ethyl acetate, toluene, chlorobenzene, tetrahydrofuran, dimethyl sulfoxide, water, and a combination thereof.

15. The method of claim 1, wherein the at least one sample is applied about 5 to 10 mm from the bottom of the chip.

16. The method of claim 1, wherein the SERS spectra are obtained at regular intervals of about 0.25 to about 1 mm along the developing direction.

17. The method of claim 1, wherein the SERS spectra are obtained at irregular intervals along the developing direction.

18. The method of claim 1, wherein analyzing all of the SERS spectra comprises dividing the peak intensities obtained at intervals each by the highest peak intensity to yield a series of normalized peak intensities, wherein the series of normalized peak intensities are plotted against a developing distance.

19. The method of claim 1, wherein the at least one analyte is separated by the UTLC and wherein the at least one analyte is identified based on its signature SERS peak.

20. A method of separating and identifying at least one component in a mixture comprising:
   applying the mixture to a SERS-active UTLC chip, wherein the SERS active UTLC chip comprises an array of Ag nanorods on a surface of a substrate, wherein a tilt angle β between an individual nanorod and the substrate surface is less than about 90 degrees;
   acquiring at least one SERS spectra at the origin of application;
   immersing the SERS-active UTLC chip into a mobile phase solvent;
   developing the chip so that the components in the mixture are separated and retained at different locations on the chip as a result of their different affinities to the Ag nanorods and solvent;
   acquiring at least one SERS spectra at intervals along the development direction; and
   analyzing all of the SERS spectra to identify the at least one component.

21. The method of claim 20, wherein the component is selected from the group consisting of: melamine, a contaminant, a biomarker, a polypeptide, a protein, a glycoprotein, a nucleic acid, a eukaryotic cell, a prokaryotic cell, a virus, a bacterium, a protozoa, a apicomplexan, a trematode, a nematode, a fungus, a spore, a carbohydrate, a lipid, a vitamin, a mycrotoxin, a drug, a pesticide, and a combination thereof.

22. The method of claim 20, wherein the mixture is applied about 5 to 10 mm from a bottom of the chip.

23. The method of claim 20, wherein the SERS spectra are obtained at regular intervals of about 0.25 to about 1 mm along the developing direction.

24. The method of claim 20, wherein the SERS spectra are obtained at irregular intervals along the developing direction.

\* \* \* \* \*